(12) United States Patent
Chu et al.

(10) Patent No.: US 11,603,492 B2
(45) Date of Patent: Mar. 14, 2023

(54) ULTRABRIGHT LANTHANIDE-DOPED NANOPARTICLES

(71) Applicant: The Board of Trustees of the Leland Stanford Junior University, Stanford, CA (US)

(72) Inventors: Steven Chu, Menlo Park, CA (US); Qian Liu, Mountain View, CA (US); Yunxiang Zhang, Redwood City, CA (US); Chunte Peng, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/053,301

(22) PCT Filed: May 9, 2019

(86) PCT No.: PCT/US2019/031579
§ 371 (c)(1),
(2) Date: Nov. 5, 2020

(87) PCT Pub. No.: WO2019/217721
PCT Pub. Date: Nov. 14, 2019

(65) Prior Publication Data
US 2022/0041926 A1 Feb. 10, 2022

Related U.S. Application Data

(60) Provisional application No. 62/669,630, filed on May 10, 2018, provisional application No. 62/669,100, filed on May 9, 2018.

(51) Int. Cl.
*C09K 11/77* (2006.01)
*C09K 11/02* (2006.01)

(52) U.S. Cl.
CPC ........ *C09K 11/7705* (2013.01); *C09K 11/025* (2013.01); *C09K 11/7773* (2013.01)

(58) Field of Classification Search
CPC .............. C09K 11/7705; C09K 11/772; C09K 11/7733; C09K 11/7748
See application file for complete search history.

(56) References Cited

U.S. PATENT DOCUMENTS

2013/0115172 A1 5/2013 Jang
2016/0122635 A1* 5/2016 Liu ........................... G01J 1/58
250/473.1
(Continued)

FOREIGN PATENT DOCUMENTS

CN 104232091 12/2014

OTHER PUBLICATIONS

Teitelboim. Upconversion in quantum dot-quantum well heterostructures. ACS Nano 2016. 10, 446-452 (Year: 2016).*
(Continued)

*Primary Examiner* — Matthew E. Hoban
(74) *Attorney, Agent, or Firm* — Lumen Patent Firm

(57) ABSTRACT

An upconversion single molecule probe is provided that includes a core having a nanoparticle seed crystal, where the nanoparticle seed crystal is an upconversion seed crystal, a first shell enveloping the core, and a second shell enveloping the first shell.

10 Claims, 19 Drawing Sheets

(56) References Cited

U.S. PATENT DOCUMENTS

2018/0303959 A1* 10/2018 Jang .................. A61K 49/0019
2019/0001024 A1* 1/2019 Grubbs ................ A61F 2/1627

OTHER PUBLICATIONS

Su. The effect of surface coating on energy migration-mediated upconversion. J. Am. Chem. Soc 2012, 134, 20849-20857 (Year: 2012).*

Gargas. Engineering bright sub-10-nm upconverting nanocrystals for single-molecule imaging. Nature Nanotechnology. vol. 9 Apr. 2014, 300-305. (Year: 2014).*

Huang. Understanding the effect of Mn2+ on Yb3+/Er3+ upconversion and obtaining a maximum upconversion fluorescence enhancement in inert-core/active-shell/inert-shell structure. RSC Adv., 2016,6, 83321-83327 (Year: 2016).*

Yi et al. Water-Soluble NaYF4:Yb,Er(Tm)/NaYF4/Polymer Core/Shell/Shell Nanoparticles with Significant Enhancement of Upconversion Fluorescence, Chemistry of Materials 2007 19 (3), 341-343 DOI: 10.1021/cm062447y.

* cited by examiner

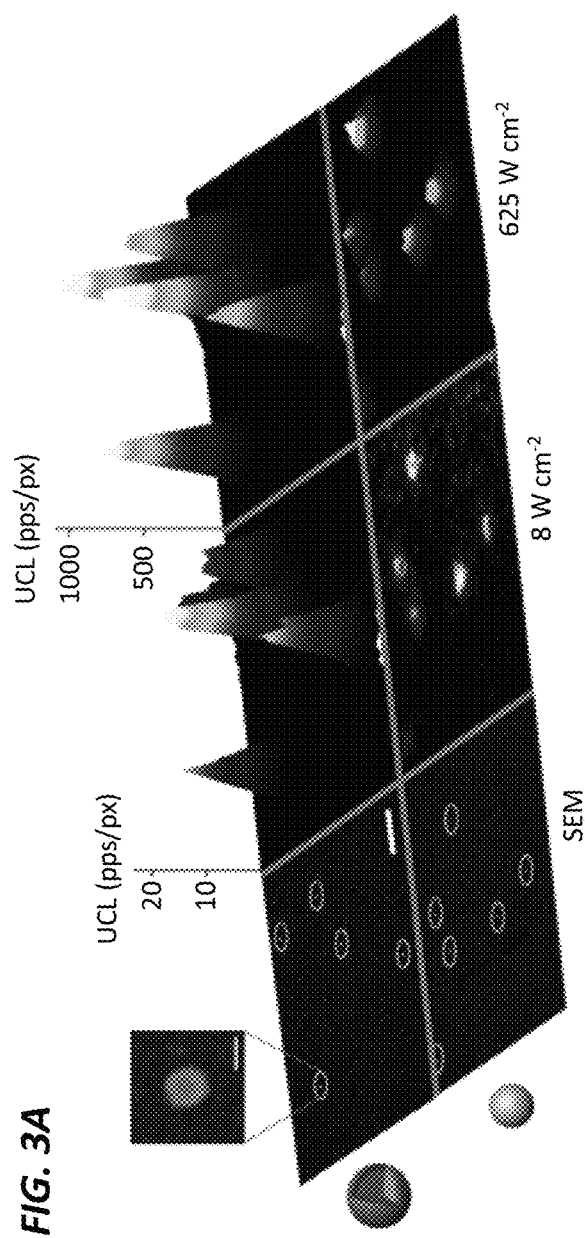
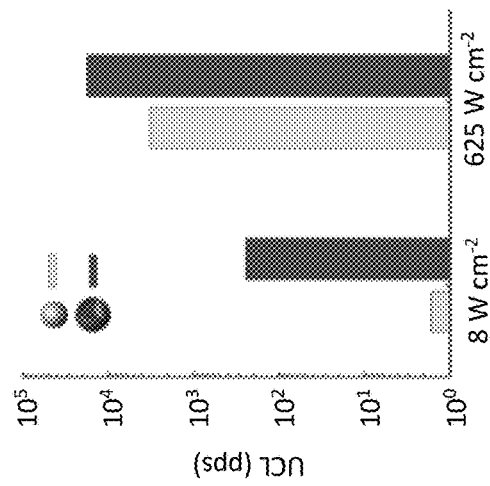
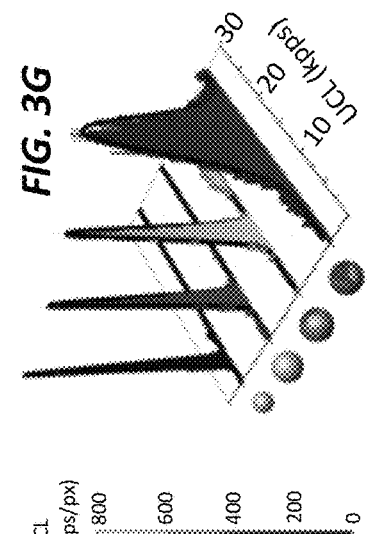
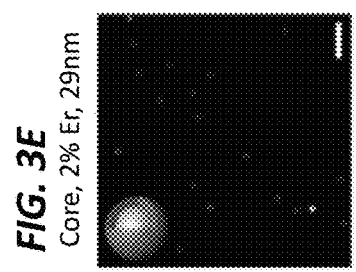
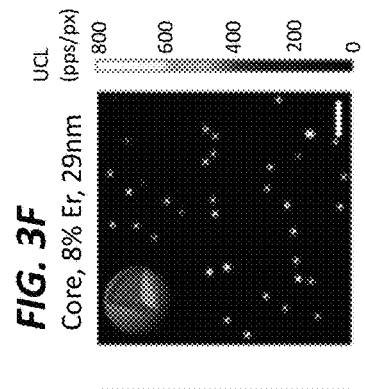
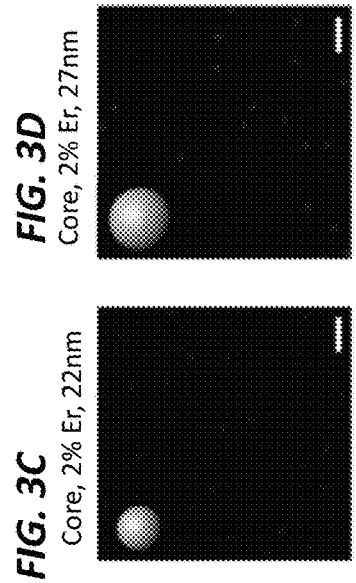

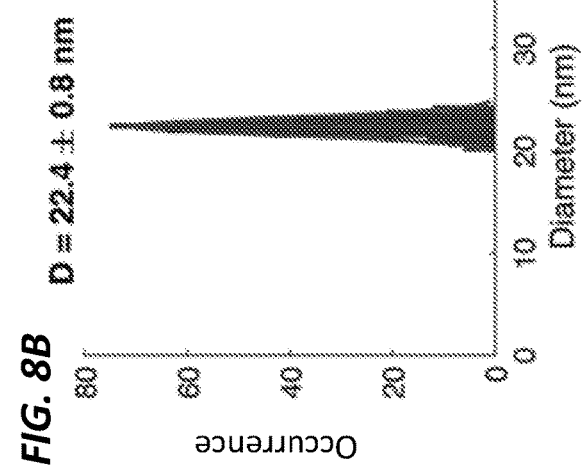
FIG. 8A
FIG. 8B
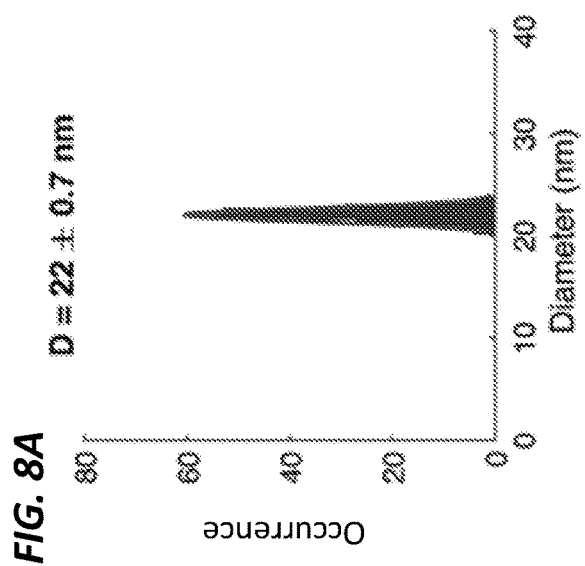
FIG. 8C
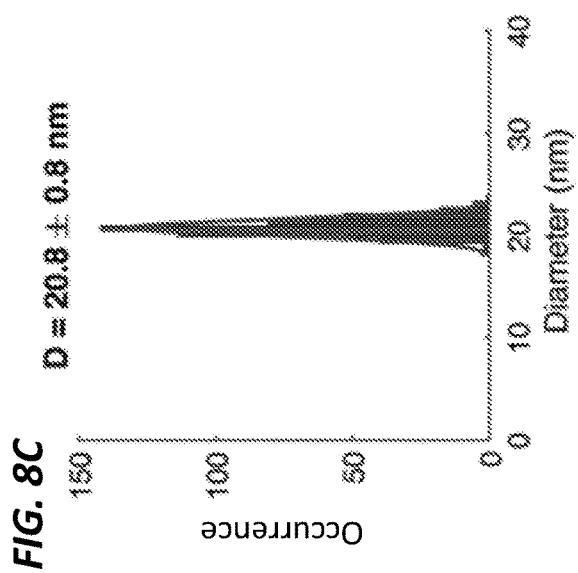
FIG. 8D
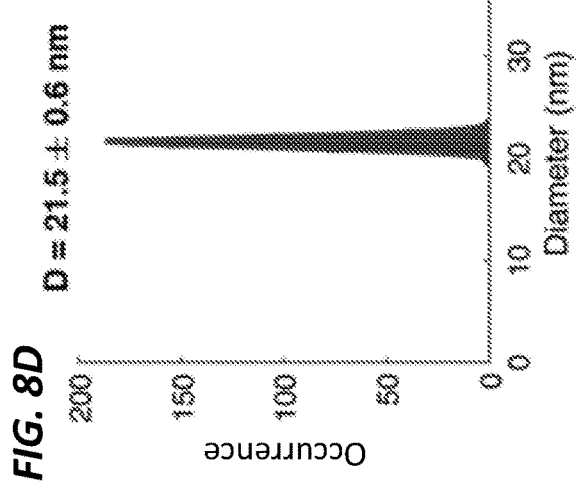

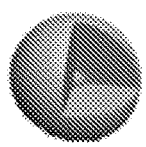
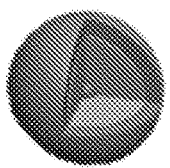
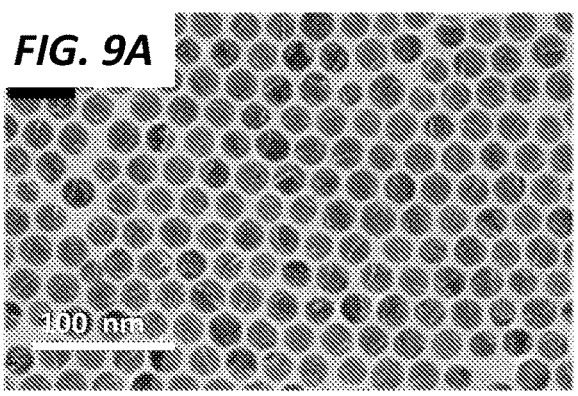
FIG. 9A
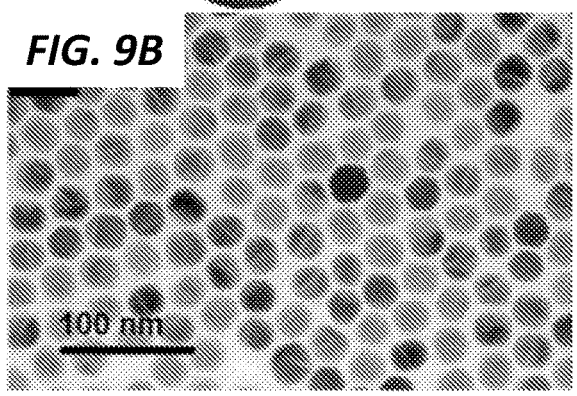
FIG. 9B
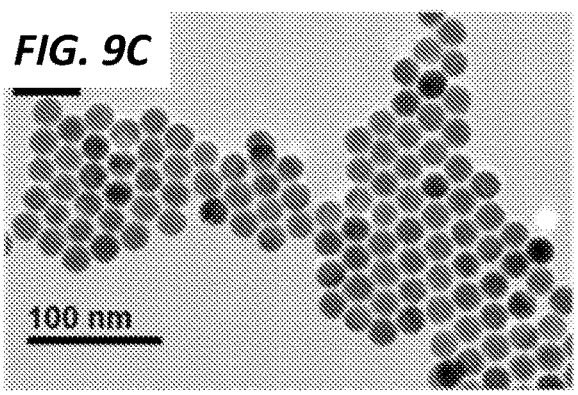
FIG. 9C
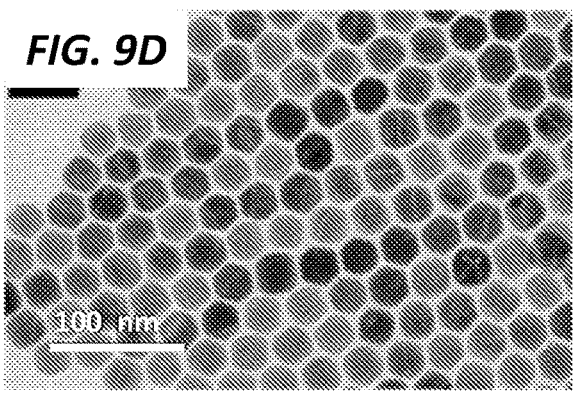
FIG. 9D
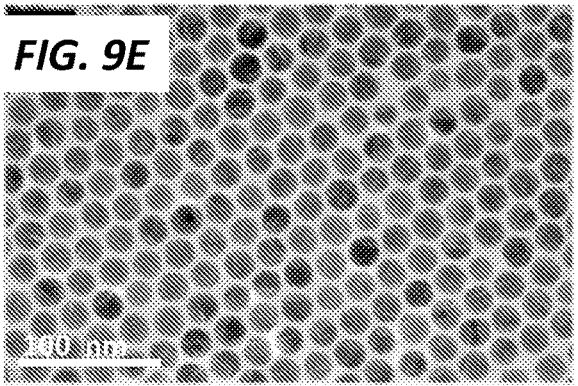
FIG. 9E
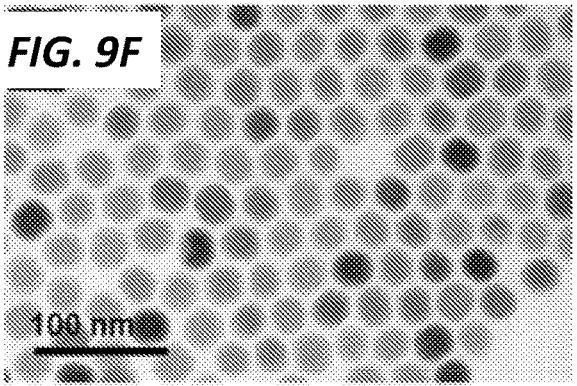
FIG. 9F
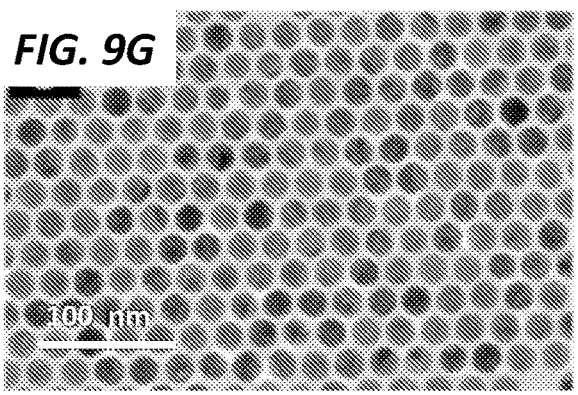
FIG. 9G
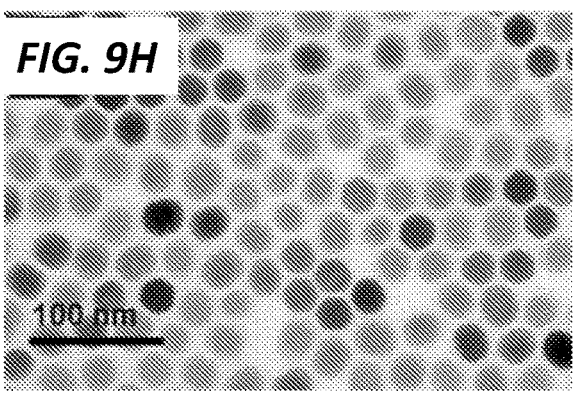
FIG. 9H

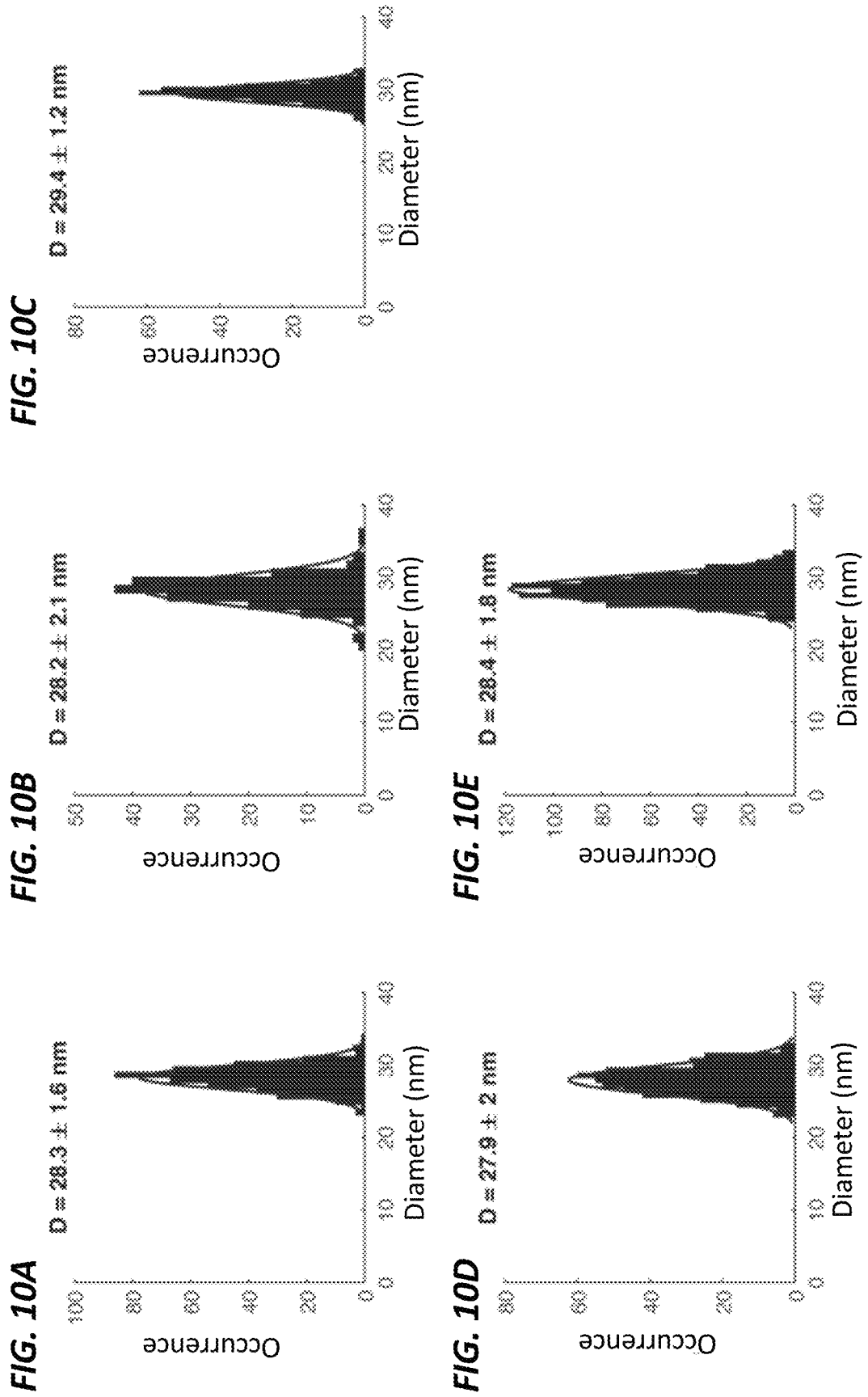

ULTRABRIGHT LANTHANIDE-DOPED NANOPARTICLES

FIELD OF THE INVENTION

The present invention relates generally to single-molecule fluorescent probes. More particularly, the invention relates to a core-shell-shell (CSS) structure of upconversion nanoparticles developed for single-molecule luminescence imaging.

BACKGROUND OF THE INVENTION

Optical upconversion uses two or more near-infrared photons in a multiple-step excitation process to generate emission at shorter wavelengths. This luminescence offers many applications including nearly background-free imaging, optical sensing, multicolor displays and photovoltaics. In particular, lanthanide-doped upconversion nanoparticles (UCNPs) have emerged as important luminescent particles for bio-imaging and photovoltaic applications due to their exceptional optical properties such as photostability, non-blinking, large anti-Stokes shifts and sharp emission lines. These advantages of UCNPs over conventional fluorescent probes such as fluorescent proteins and organic dyes can potentially open up a wide range of applications such as long-term single molecule tracking in live cells and organisms.

Despite many desirable optical properties of UCNPs, one of the major hurdles in the application of UCNPs as single-molecule biological probes is their weak luminescence. To date, reliable single-particle imaging of UCNPs have required high illumination power density in the range of 10 kW cm$^{-2}$ to 10 MW cm$^{-2}$. However, prolonged illumination with 980 nm light at these intensities is known to induce photodamage in cells. Enhancing the luminescence of UCNPs can utilize strategies such as optimizing the host matrix and increasing sensitizer or activator ions. UCNPs are composed of host matrix, sensitizer and emitter. The hexagonal phase $NaYF_4$ host results in the brightest upconversion, and $Yb^{3+}$ is the most common sensitizer because its low lying optical cross-section is concentrated into a single $^2F_{7/2} \rightarrow ^2F_{5/2}$ transition, which can be used to step-wise excite the emitter ions such as $Er^{3+}$, $Tm^{3+}$, and $Ho^{3+}$ through rapid energy.

In order to optimize the optical properties of UCNPs, it is necessary to systematically tune the size of the nanoparticle, as well as adjusting the type of ion and the concentration of the sensitizer and emitters while keeping the nanoparticle volume unchanged for a fair comparison between different formulations. However, controllable synthesis of UCNPs remains a technical challenge. For instance, increasing the sensitizer $Yb^{3+}$ amount in UCNPs (in order to increase the 980 nm absorption) from 30% to 60% molar ratio results in an increase of the size of the nanoparticles from 27.4 nm to 51.3 nm[13]. On the other hand, $Gd^{3+}$ doping could reduce the $NaYF_4$ size down to 10 nm.

Previously, the nanoparticle size was tuned by adjusting the synthesis formulation such as changing the amount of surfactant (oleic acid or sodium oleate), or the amount of chemicals containing Na and F. However, this strategy is limited by its non-generality. The recipe needs to be re-optimized every time when changing the doping ratio of lanthanide ion, resulting in a time- and energy-consuming process.

What is needed is a core-shell-shell (CSS) structure of upconversion nanoparticles and a method of fabrication for single-molecule luminescence imaging.

SUMMARY OF THE INVENTION

To address the needs in the art, an upconversion single molecule probe is provided that includes a core having a nanoparticle seed crystal, where the nanoparticle seed crystal is an upconversion seed crystal, a first shell enveloping the core, and a second shell enveloping the first shell.

According to one aspect of the invention, the nanoparticle seed crystal includes a $NaREF_4$ seed crystal, where the RE includes Y, Gd, Lu, Yb, Er, Tm, Ho, Pr, Nd, Eu, Tb, Dy, Ce, Sm, or La.

In another aspect of the invention, the nanoparticle seed crystal has a size in a range of 2-8 nm.

In a further aspect of the invention, the first shell includes a size-tunable and optically active $NaRE_aF_4$: x % RE first shell, where the RE includes Y, Gd, Lu, Yb, Er, Tm, Ho, Pr, Nd, Eu, Tb, Dy, Ce, Sm, or La, where the x=0-100.

According to one aspect of the invention, the first shell includes a thickness in a range of 1-50 nm.

In yet another aspect of the invention, the second shell includes an inert $NaREF_4$ second shell, where the RE includes Y, Gd, Lu, or La.

In a further aspect of the invention, the second shell includes a thickness in a range of 1-25 nm.

In one aspect the invention includes a method of fabricating an upconversion single molecule probe that includes synthesizing a core having a nanoparticle seed crystal, where the nanoparticle seed crystal is an upconversion seed crystal, synthesizing a first shell on the core, and synthesizing a second shell on the first shell, where synthesizing the nanoparticle seed includes a $NaREF_4$ seed crystal, where the RE includes Y, Gd, Lu, Yb, Er, Tm, Ho, Pr, Nd, Eu, Tb, Dy, Ce, Sm, or La.

BRIEF DESCRIPTION OF THE DRAWINGS

FIGS. 3A-3G show correlative SEM and wide-field fluorescence images of UCNPs. (3A) The left column shows the SEM images of $NaYF_4@NaYb_{0.92}F_4$: $Er_{0.08}@NaYF_4$ (top) and 22 nm $NaY_{0.78}F_4:Yb_{0.2}Er_{0.02}$ (bottom). The inset displays the zoom-in view for a single nanoparticle. Scale bars: 500 nm, and 30 nm for the inset. The middle and right columns are the 3D representation of the wide-field fluorescence images at 8 W cm$^{-2}$ and 625 W cm$^{-2}$, respectively. The z-axis, showing the luminescence intensity (photons per second per pixel), is fixed at each excitation power density. (3B) Comparison of integrated single-particle upconversion emissions. Notice that the intensity axis is in log scale. (3C-3F) Wide-field images taken at 625 W cm$^{-2}$ for core (2% Er, 22 nm), core (2% Er, 27 nm), core-shell (2% Er, 29 nm), and core-shell-shell (8% Er, 29 nm), respectively. The same color map axis was applied to all four images. Scale bar: 2 μm. (3G) Normalized histograms of the upconversion luminescence for the four types of nanoparticles shown in (3C-3F). The histograms were built with multiple field of views (FOVs) in order to get reliable statistics over hundreds of single particles. Solid line represents the Gaussian fit, according to the current invention.

FIGS. 7A-7D show TEM images of NaY$_{1-0.2-x}$F$_4$:Yb$_{0.2}$Er$_x$ (7A-7C, x=0.04, 0.08, 0.16), according to the current invention.

FIGS. 8A-8D show size distribution of NaY$_{1-0.2-x}$F$_4$:Yb$_{0.2}$Er$_x$ (8A-8D, x=0.02, 0.04, 0.08, 0.16), according to the current invention.

FIGS. 9A-9H show TEM images of NaYF$_4$@NaYb$_{1-x}$F$_4$:Er$_x$ (9A, 9C, 9E, 9G, x=0.04, 0.08, 0.16, 0.50), NaYF$_4$@NaYb$_{1-x}$F$_4$:Er$_x$@NaYF$_4$ (9B, 9D, 9F, 9H, x=0.04, 0.08, 0.16, 0.50), according to the current invention.

FIGS. 10A-10E show TEM images of NaYF$_4$@NaYb$_{1-x}$F$_4$:Er$_x$@NaYF$_4$ (a-e, x=0.02, 0.04, 0.08, 0.16, 0.50), according to the current invention.

14A-14B show (14A) UCL intensities of the three core-only UCNPs as a function of particle volume, at 1 MW cm$^{-2}$. The dash line is the linear fit to the experimental data points. (14B) Normalized UCL intensities of the three core-only UCNPs as a function of particle diameter, at 1 MW cm$^{-2}$. The dash line represents ideal volumetric scaling, according to the current invention.

Figure 15B:
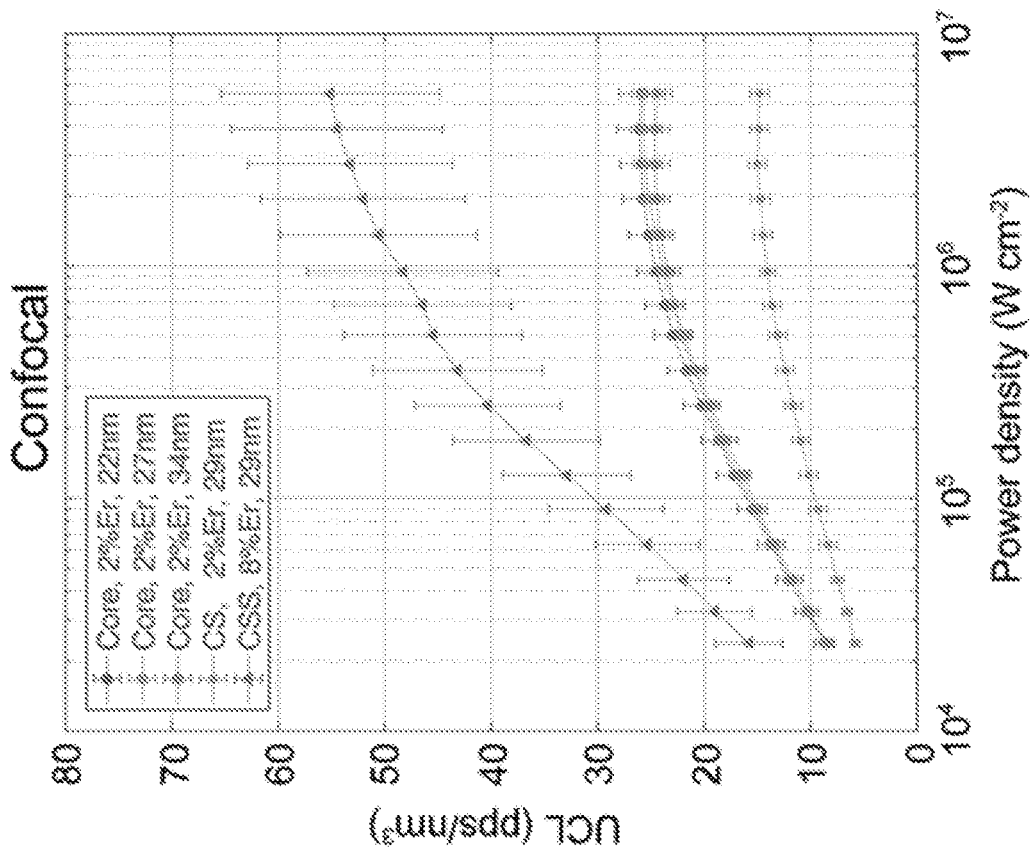
Figure 15A:
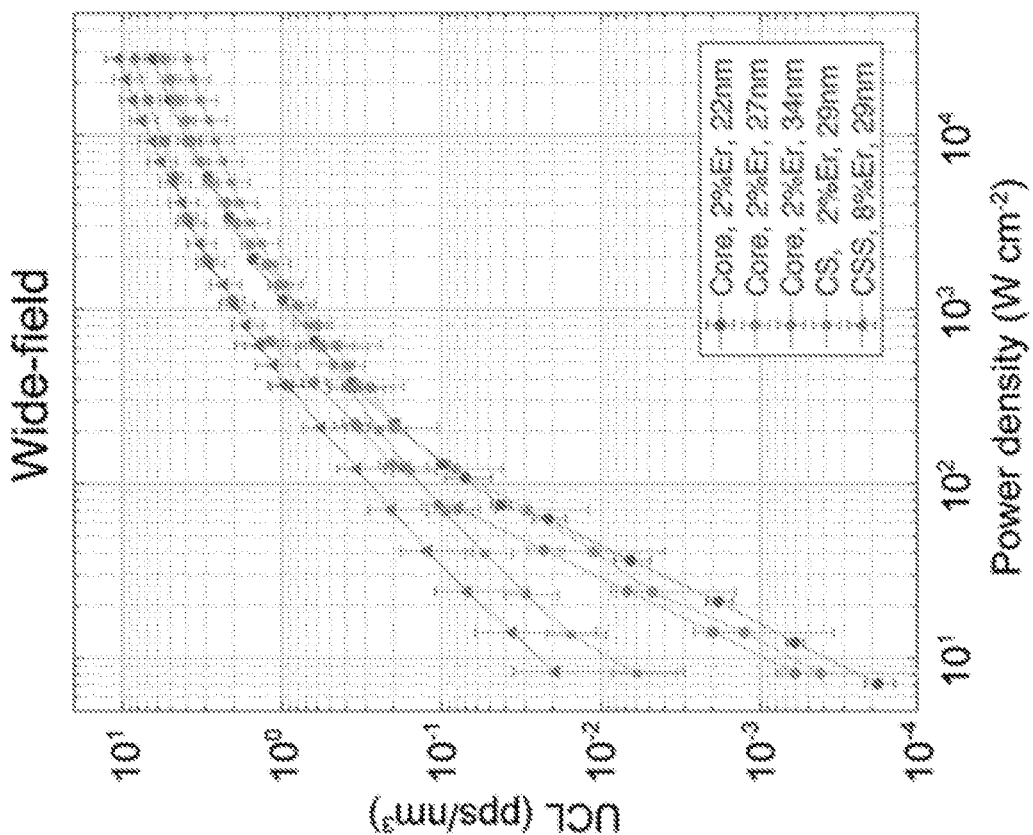

FIGS. 15A-15B show volume normalized saturation curves obtained from wide-field (15A) and confocal (15B) microscopes. The kink in the saturation curves under low power densities is due to the addition of an OD2 ND filter, according to the current invention.

Figure 16:
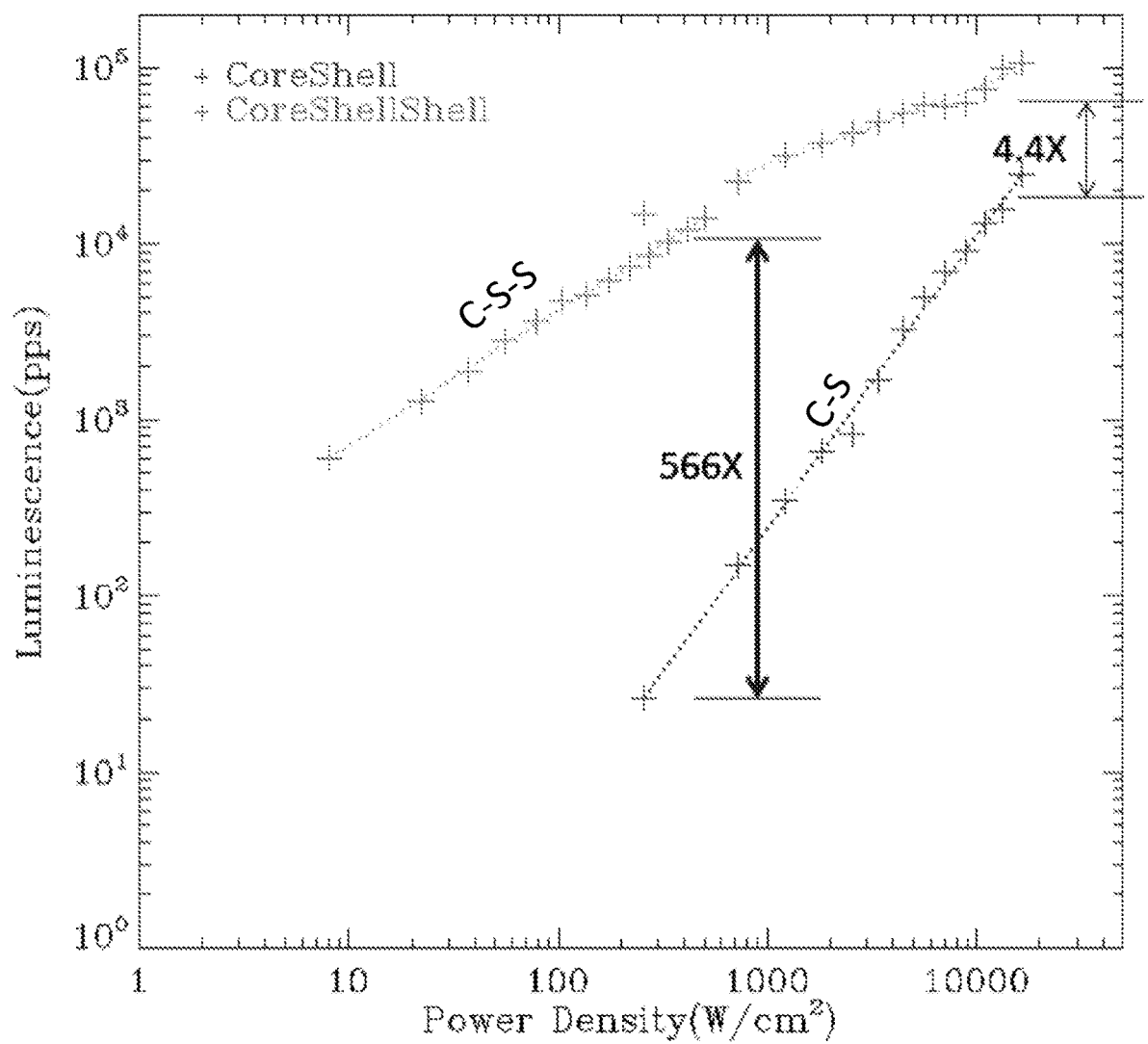
Figure 17:
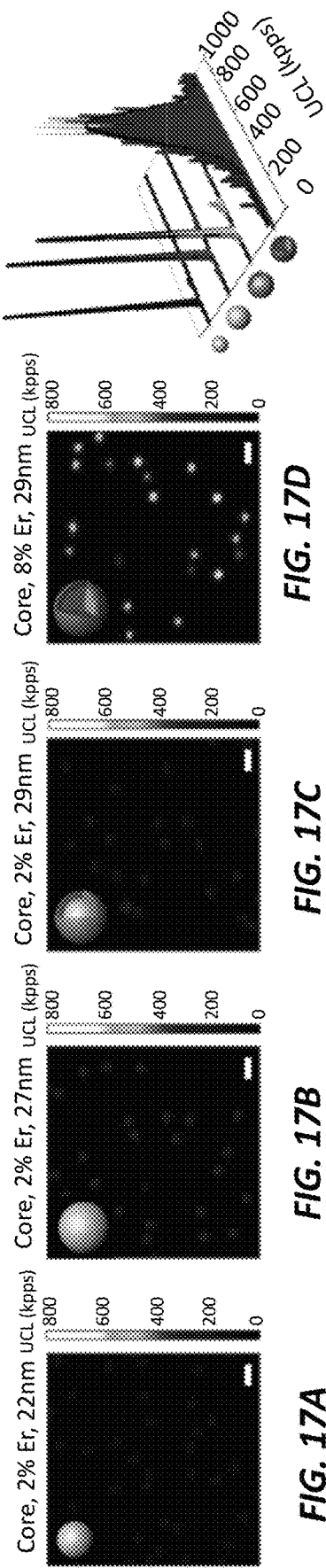

FIG. 16 shows saturation curves for NaYF$_4$@NaYb$_{0.98}$F$_4$:Er$_{0.02}$ (bottom) with no protective outer shell added, and NaYF$_4$@NaYb$_{0.98}$F$_4$:Er$_{0.02}$@NaYF$_4$ (top).

FIGS. 17A-17E show (17A-17D) Confocal images taken at 678 kW cm$^{-2}$ for NaY$_{0.78}$F$_4$:Yb$_{0.2}$Er$_{0.02}$ (17A, 22.0 nm; 17B, 27.1 nm), and NaY$_{0.78}$F$_4$:Yb$_{0.2}$Er$_{0.02}$@NaYF$_4$ (17C, 29.1 nm) and core-shell-shell NaYF$_4$@NaYb$_{0.92}$F$_4$:Er$_{0.08}$@NaYF$_4$ (17D, 29.4 nm), respectively. The same colormap axis was applied to all four images. Scale bar: 2 μm. (17E) Normalized histograms of the upconversion luminescence (UCL) for the four types of nanoparticles shown in (17A-17D). The histograms were built with multiple FOVs in order to get reliable statistics over hundreds of single particles. Solid line represents the Gaussian fit, according to the current invention.

Figure 18:
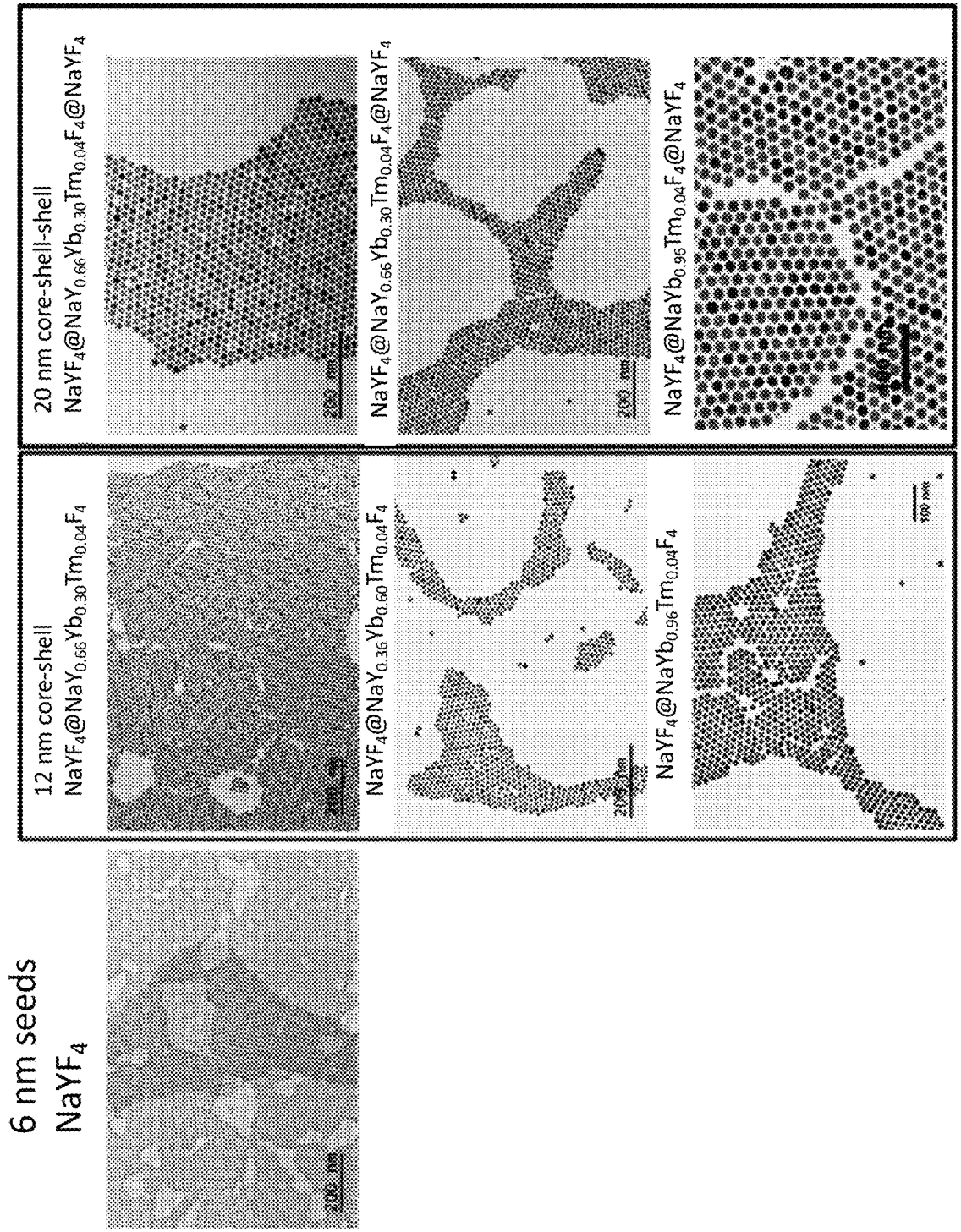
Figure 19:
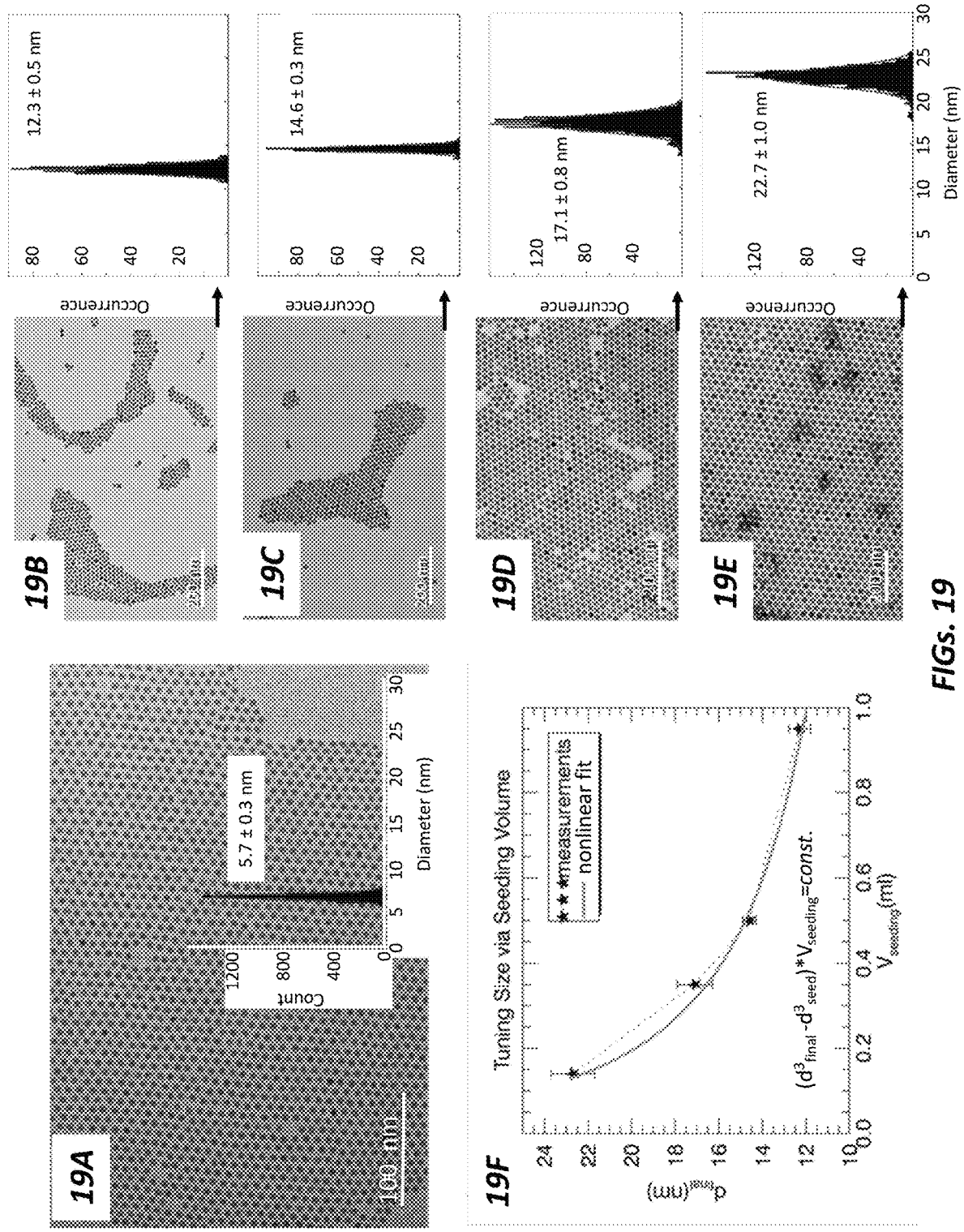

FIG. 18 shows TEM images of 6 nm NaYF$_4$ seeds, 12 nm NaYF$_4$@NaY$_x$Yb$_{0.96-x}$F$_4$:Tm$_{0.04}$ and 20 nm NaYF$_4$@NaY$_x$Yb$_{0.96-x}$F$_4$:Tm$_{0.04}$@NaYF$_4$ (x=0, 0.36, 0.66), according to the current invention.

FIGS. 19A-19E shows TEM images of NaYF$_4$ core (19A) and core-shell NaYF$_4$@NaYb$_{0.92}$F$_4$:Er$_{0.08}$ with different size (19B-19E), (19D) Final core-shell size as a function of the used core seeding volume and nonlinear fitting, according to the current invention.

DETAILED DESCRIPTION

Lanthanide-doped upconversion nanoparticles (UCNPs) are promising single-molecule probes given their non-blinking, photobleach-resistant luminescence upon infrared excitation. However, the weak luminescence of sub-50 nm UCNPs limits their single-particle detection to above 10 kWcm$^{-2}$ that is unpractical for live cell imaging. According to one aspect of the invention, single-particle luminescence is systematically characterized for UCNPs with various formulations over a 10$^6$ variation in incident power, down to 8 Wcm$^{-2}$. A core-shell-shell (CSS) structure (NaYF$_4$@NaYb$_{1-x}$F$_4$:Er$_x$@NaYF$_4$) is shown to be significantly brighter than the commonly used NaY$_{0.78}$F$_4$:Yb$_{0.2}$Er$_{0.02}$. At 8 Wcm$^{-2}$, the 8% Er$^{3+}$ CSS particles exhibit a 150-fold enhancement given their high sensitizer Yb$^{3+}$ content and the presence of an inert shell to prevent energy migration to defects. Moreover, revealed herein is a power-dependent luminescence enhancement from the inert shell, which explains the unmatched enhancement factors reported by ensemble and previous single-particle measurements. These brighter probes open the possibility of cellular and single-molecule tracking at low irradiance.

In order to systemically optimize the upconversion luminescent brightness of UCNPs, a combination of wide-field and confocal microscopy have been employed to characterize a set of UCNPs at the single-particle level with laser power density between 8 W cm$^{-2}$ to 6 MW cm$^{-2}$. Described herein is the effect of particle size, the addition of an inactive shell, and variations in the concentration of activator. More importantly, to explore the possibility of luminescence enhancement with higher Yb$^{3+}$ content, the properties of a new core-shell-shell structure (NaYF$_4$@NaYb$_{1-x}$F$_4$:Er$_x$@NaYF$_4$) have been synthesized and measured.

Figure 5:
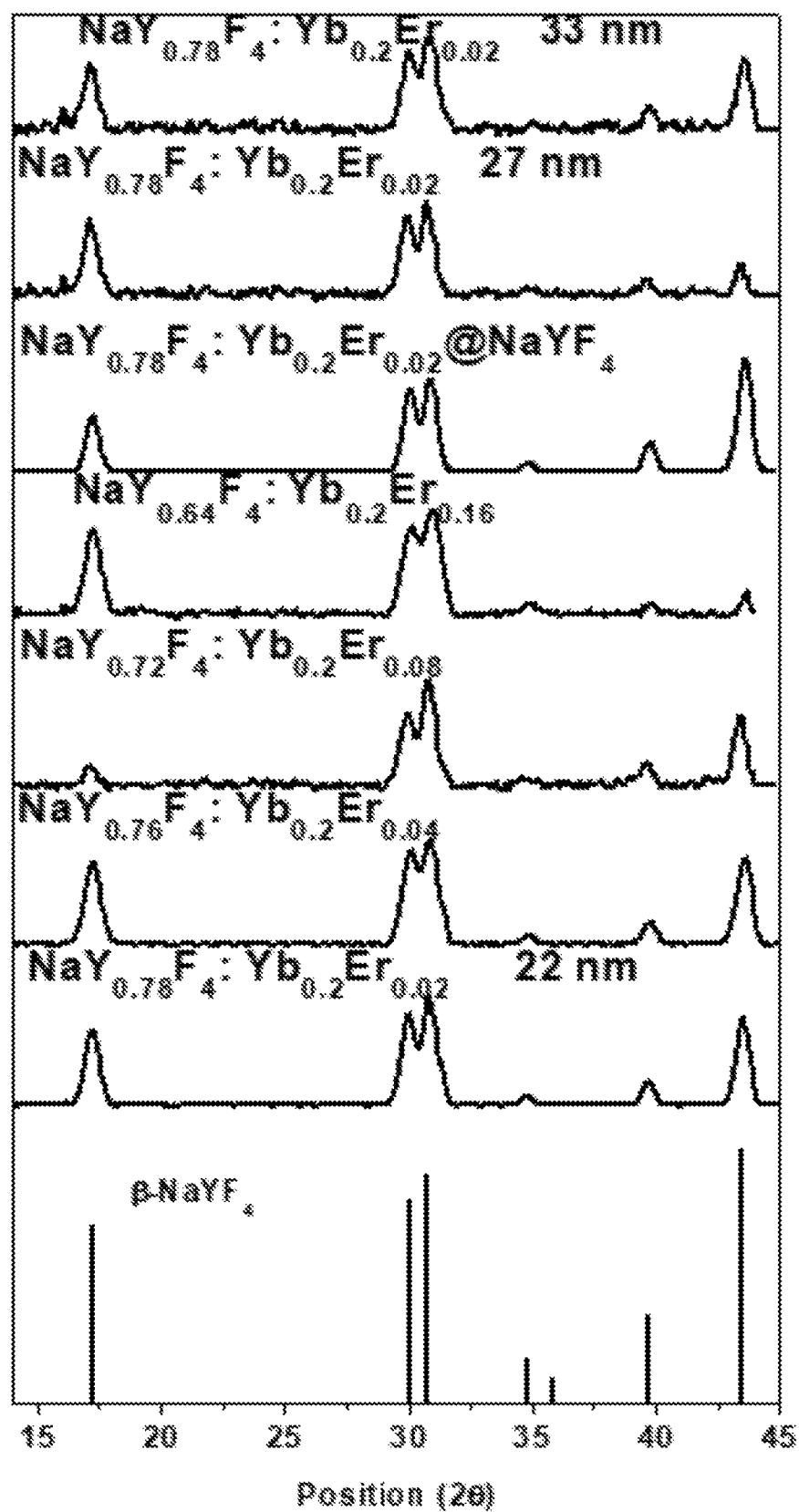
FIG. 5 shows XRD of NaY$_{0.78}$F$_4$:Yb$_{0.2}$Er$_{0.02}$ (with diameters of 22 nm, 27 nm, and 33 nm), NaY$_{1-0.2-x}$F$_4$:Yb$_{0.2}$Er$_x$ (x=0.04, 0.08, 0.16), core-shell NaY$_{0.78}$F$_4$:Yb$_{0.2}$Er$_{0.02}$@NaYF$_4$, and standard hexagonal-phase NaYF$_4$. The variation of the peak ratios in different samples could be the result of different crystal orientations. It is challenging to control the preferred orientation during sample preparation, but the characteristic peaks can still be used to confirm the crystal phase, according to the current invention.
Figure 6A:
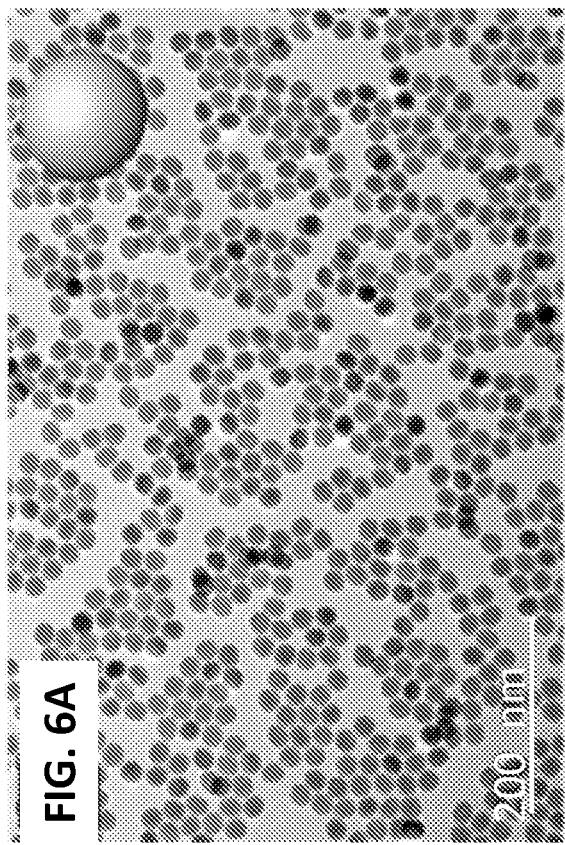
FIGS. 6A-6D show TEM images of the as-prepared NaY$_{0.78}$F$_4$:Yb$_{0.2}$Er$_{0.02}$ (6A, 22 nm diameter; 6B, 27 nm; 6C, 33 nm) and core-shell NaY$_{0.78}$F$_4$:Yb$_{0.2}$Er$_{0.02}$@NaYF$_4$ (6D, 29 nm), according to the current invention.
Figure 6B:
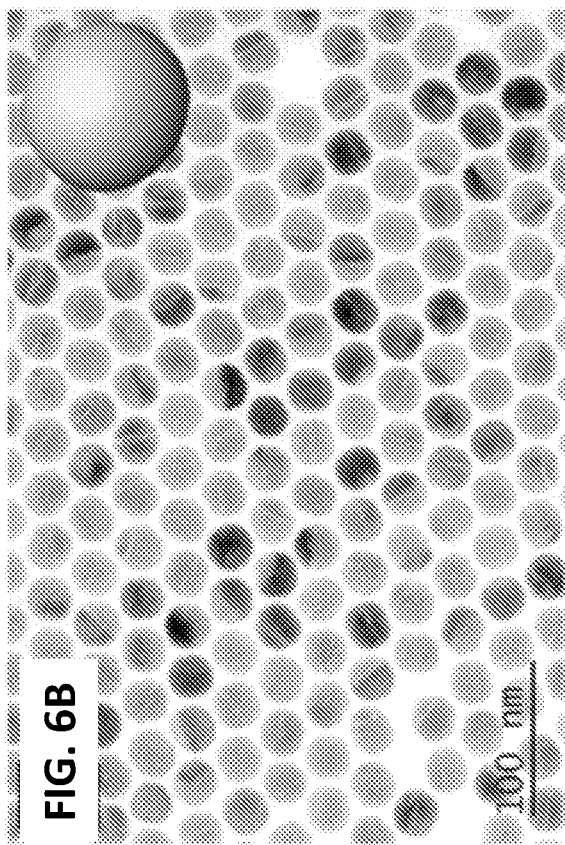

In one aspect, a solvent thermal method was used to synthesize a series of UCNPs with modifications to the most widely used Er$^{3+}$-emissive UCNPs (NaY$_{0.78}$F$_4$:Yb$_{0.2}$Er$_{0.02}$, FIG. 5) in the hexagonal phase—the best crystal structure for upconversion luminescence. The transmission electron microscopy (TEM) images showed a uniform and monodispersed morphology (FIG. 6A), with the size of 22.0±0.7 nm (FIG. 8A).

Figure 1A:
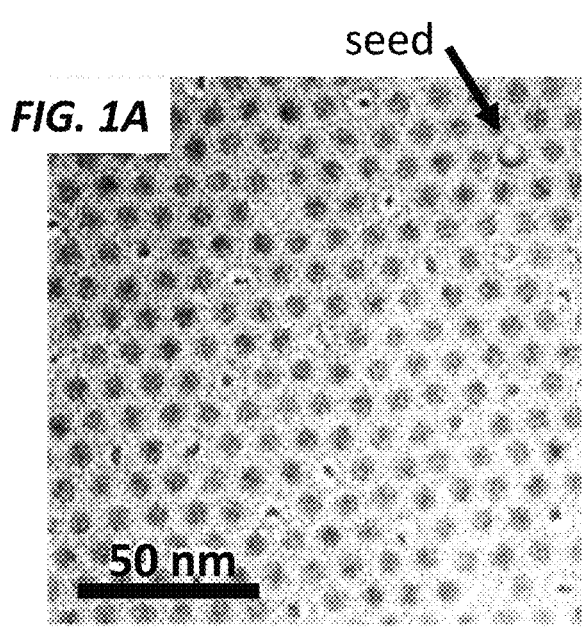
FIGS. 1A-1F show structural characterizations of core-shell-shell $NaYF_4@NaYb_{0.98}F_4$: $Er_{0.02}@NaYF_4$ UCNPs. TEM images of (1A) seed $NaYF_4$, (1B) $NaYF_4@NaYb_{0.98}F_4:Er_{0.02}$, and (1C) core-shell-shell $NaYF_4@NaYb_{0.98}F_4:Er_{0.02}@NaYF_4$. (1D) Size distributions at different stages during core-shell-shell nanoparticle synthesis. (1E) High-resolution TEM image and (1F) EDX elemental mapping of core-shell-shell $NaYF_4@NaYb_{0.98}F_4$: $Er_{0.02}@NaYF_4$, according to the current invention.
Figure 1B:
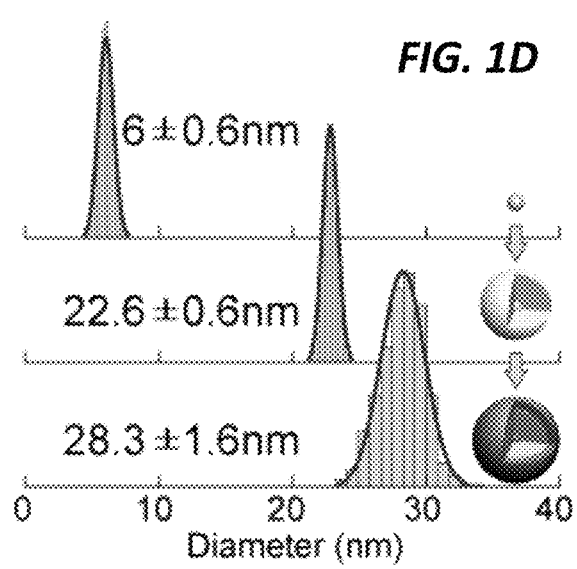
Figure 1C:
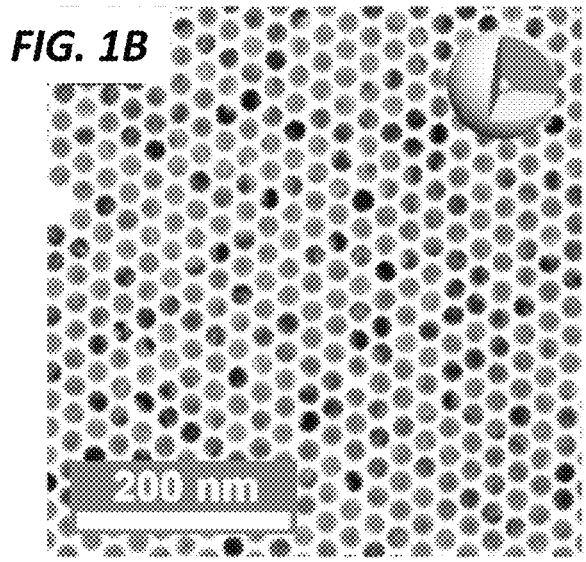
Figure 1D:
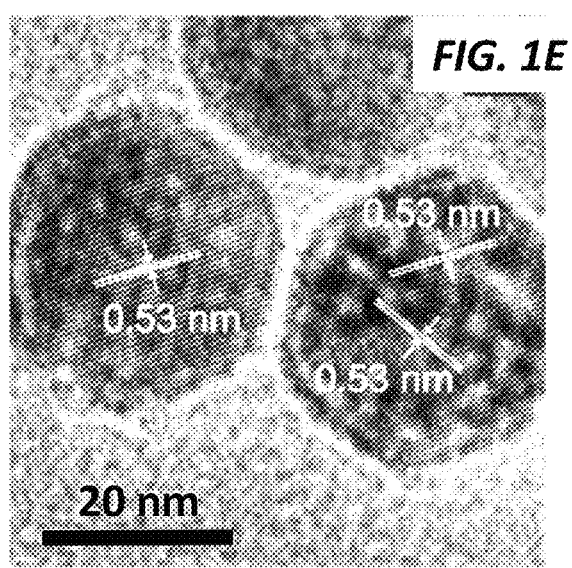
Figure 1E:
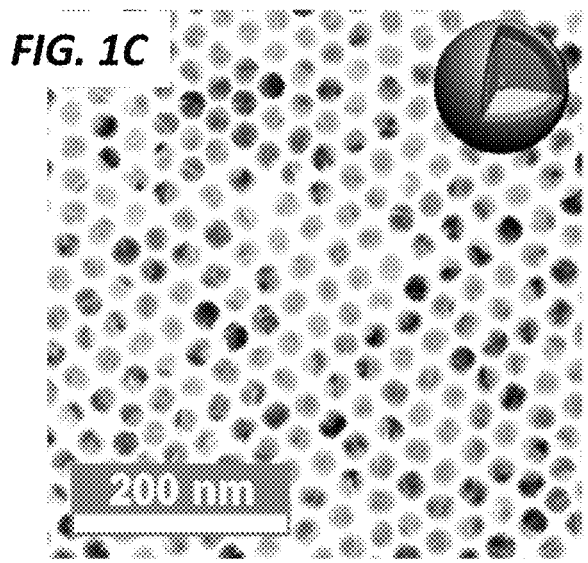

The low lying optical cross-section of Yb$^{3+}$ is concentrated into a single $^2F_{7/2} \rightarrow {}^2F_{5/2}$ transition, and rapid energy transfer among Yb$^{3+}$ ions is used to step-wise excite Er$^{3+}$ ions. An obvious choice to create the most optically active UCNPs would be to synthesize a nanocrystal with an admixture of Yb$^{3+}$ and Er$^{3+}$ ions that contains no optically inactive Y ions. However, controllable synthesis of small (<30 nm) β-NaYbF$_4$ by one-step reaction remains a challenging task. In order to create size-tunable, Yb-rich nanoparticles with high crystal quality, 6.0±0.6 nm diameter NaYF$_4$ seed crystals were first synthesized (FIG. 1A, and FIG. 1D) that allow epitaxial growth of size-tunable p-NaYbF$_4$. Having the same optically-active volume is required for a fair comparison of brightness between nanoparticles with different formulations. Therefore, a series of NaYF$_4$@NaYb$_{1-x}$F$_4$:Er$_x$ (x=0.02, 0.04, 0.08, 0.16, and 0.5) core-shell nanoparticles with all particles of uniform size ~22 nm were synthesized (FIG. 1B, FIG. 1D, FIGS. 9A-9H and FIGS. 10A-10E), which can be compared to the 22 nm core-only NaY$_{0.78}$F$_4$:Yb$_{0.2}$Er$_{0.02}$. Note that the 6 nm seed crystal represents only 2% loss of the active luminescence volume.

Figure 1F:
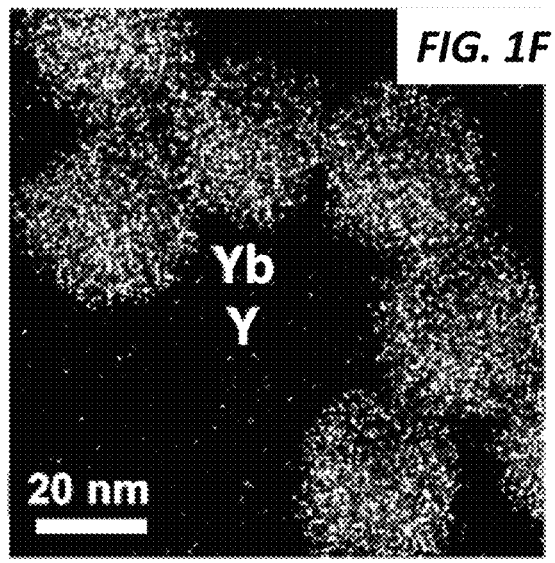
Figure 13:
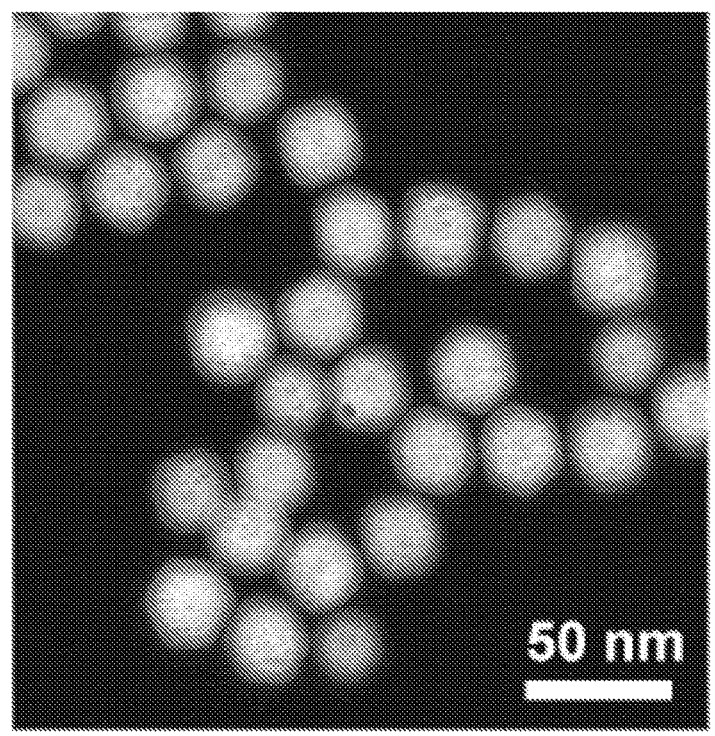
FIG. 13 shows high-angle Annular Dark-field Scanning Transmission Electron Microscopy image of core-shell-shell NaYF$_4$@NaYb$_{0.98}$F$_4$:Er$_{0.02}$@NaYF$_4$, according to the current invention.

Finally, it is well documented that high concentrations of sensitizer or activators can lead to concentration-quenching and hence decreased luminescence. Non-radiative energy loss can be alleviated by growing an epitaxial shell that reduces the resonant energy transfer among Yb$^{3+}$ ions to the surface defects and to vibrational modes of the surrounding solvent. For this reason, a final inert NaYF$_4$ shell (~3 nm thickness) was added. The resulting core-shell-shell p-phase NaYF$_4$@NaYb$_{1-x}$F$_4$:Er$_x$@NaYF$_4$ UCNPs has an overall size of around 28 nm (FIGS. 1C-1E, FIG. 9, FIG. 10, and FIG. 12). Scanning Transmission Electron Microscopy (STEM) and energy dispersive x-ray (EDX) mapping confirmed the presence of the Yb-rich core and the NaYF$_4$ shell (FIG. 1F and FIG. 13).

Figure 6C:
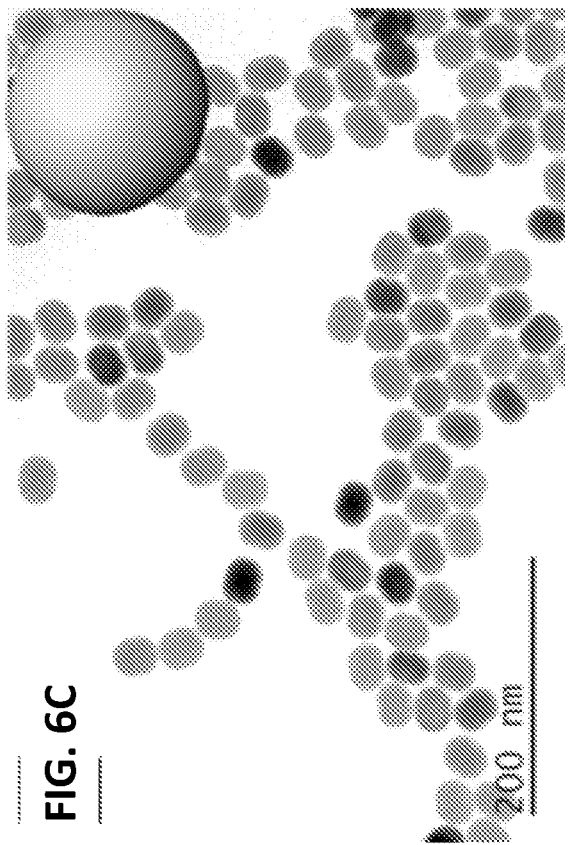
Figure 6D:
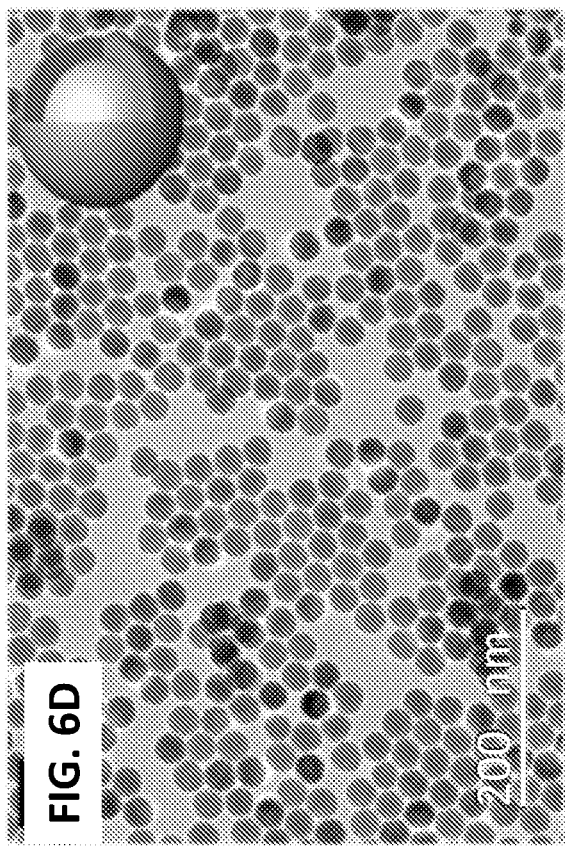
Figures 6E, 6F, 6G:
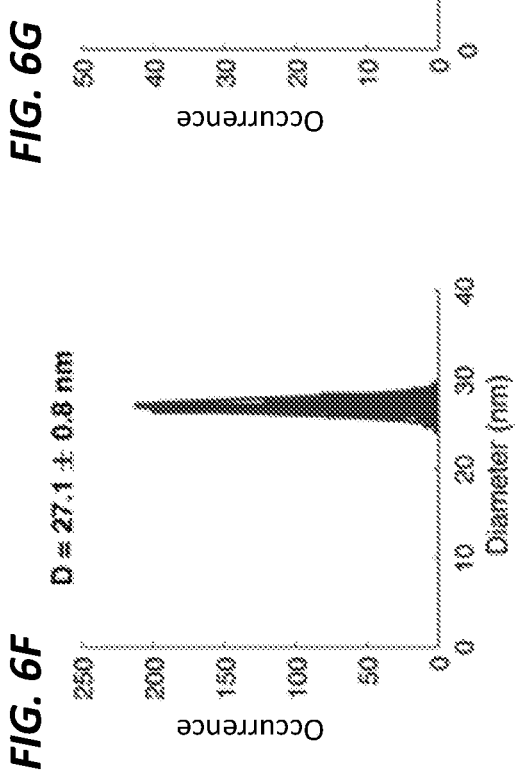
FIGS. 6E-6H show size distribution of the as-prepared NaY$_{0.78}$F$_4$:Yb$_{0.2}$Er$_{0.02}$ (6E, 22 nm; 6F, 27 nm; 6G, 33 nm) and core-shell NaY$_{0.78}$F$_4$:Yb$_{0.2}$Er$_{0.02}$@NaYF$_4$ (6H, 29 nm), according to the current invention.
Figure 6H:
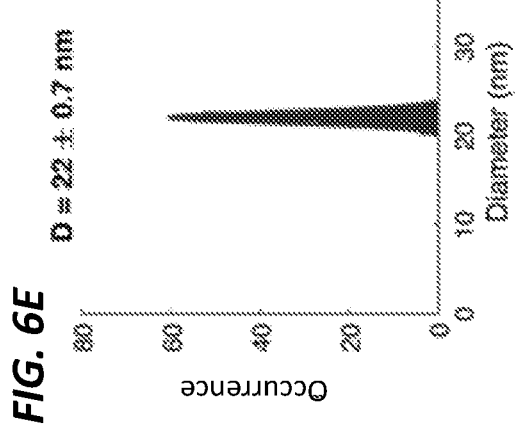
Figure 7B:
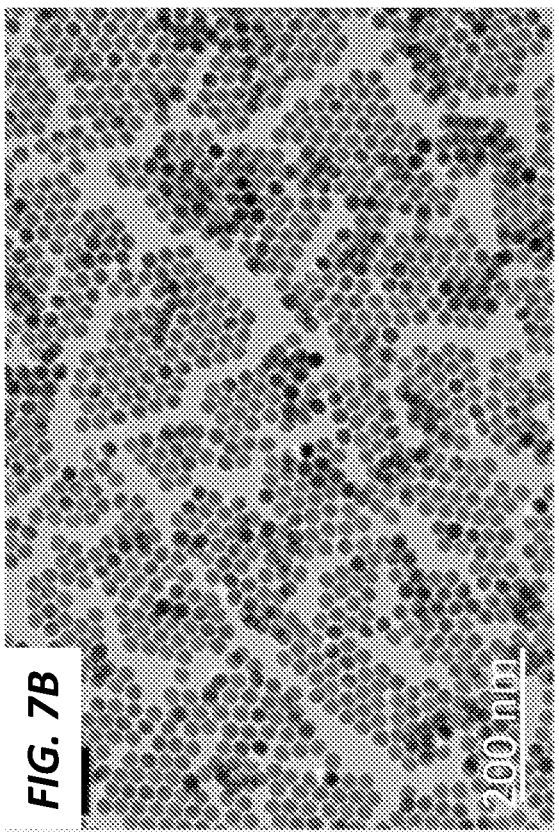
Figure 7A:
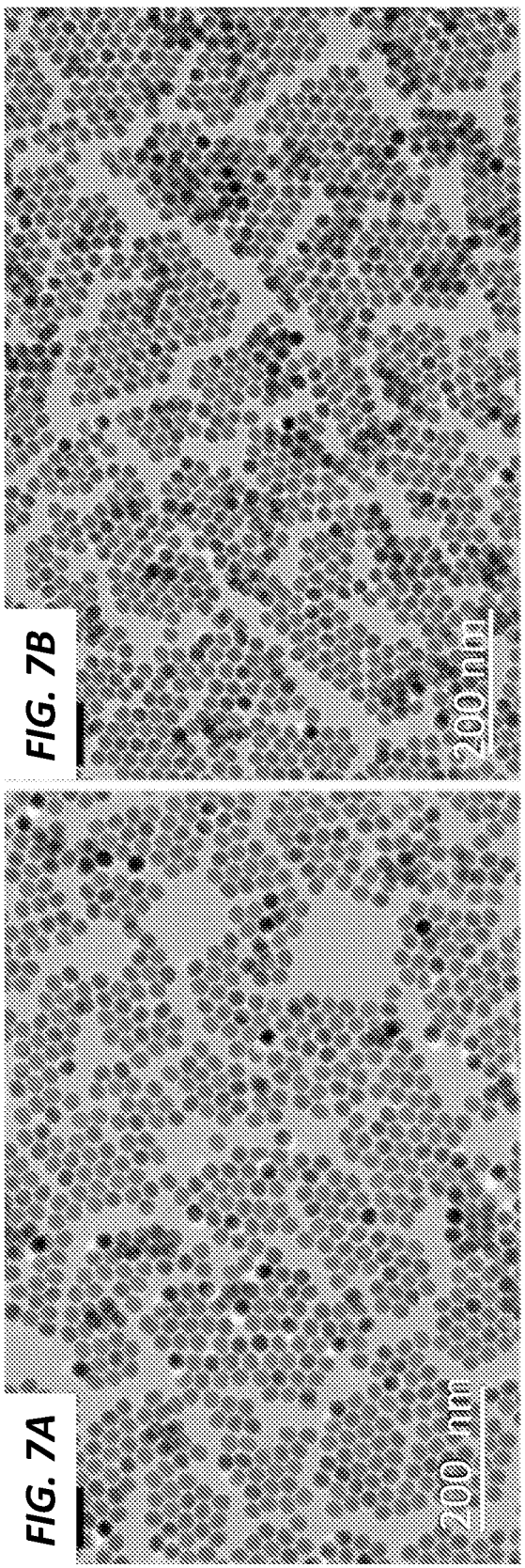
Figure 7C:
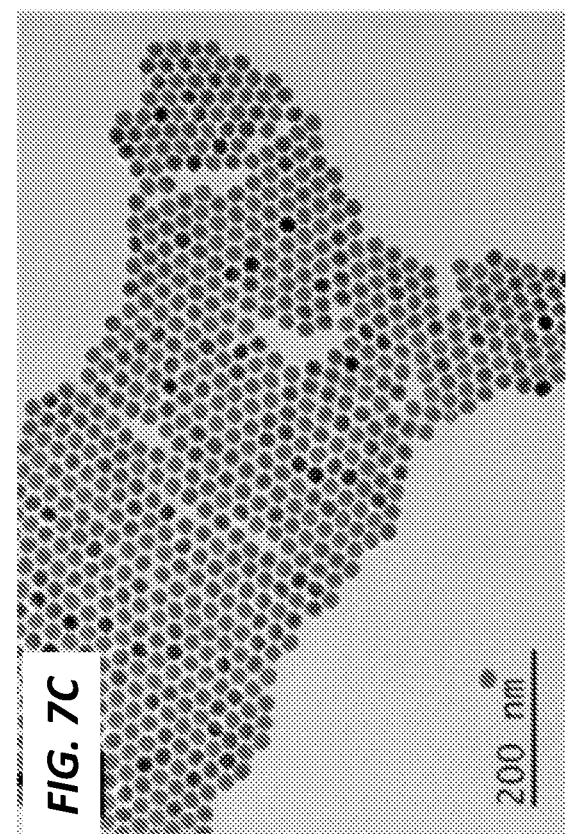

Surface quenching significantly reduces the brightness of UCNPs, especially for smaller particles whose emission intensity no longer follows ideal volumetric scaling. Consequently, two additional core-only NaY$_{0.78}$F$_4$:Yb$_{0.2}$Er$_{0.02}$ UCNPs with varying sizes were characterized: one close in size with the core-shell-shell structure (27.1±0.8 nm, FIG. 6B and FIGS. 8A-8D) and another larger UCNPs (33.6±0.7 nm, FIG. 6C and FIG. 8C). In order to suppress surface quenching, the canonical core-shell NaY$_{0.78}$F$_4$:Yb$_{0.2}$Er$_{0.02}$@NaYF$_4$ was also synthesized by growing an inert NaYF$_4$ shell on the 22 nm core-only UCNPs, giving an overall size of 29.1±1.0 nm (FIG. 6D and FIG. 8D). Moreover, to examine the effect of the activator concentration, a set of ~22 nm core-only UCNPs were made with increasing Er$^{3+}$ doping level from 2% to 16% while keeping the Yb$^{3+}$ concentration at 20% (FIG. 5, FIG. 6A, FIG. 8A and FIGS. 9A-9D).

FIGS. 6E-6H show size distribution of the as-prepared NaY$_{0.78}$F$_4$:Yb$_{0.2}$Er$_{0.02}$ (6E, 22 nm; 6F, 27 nm; 6G, 33 nm) and core-shell NaY$_{0.78}$F$_4$:Yb$_{0.2}$Er$_{0.02}$@NaYF$_4$ (6H, 29 nm), according to the current invention.

Figure 2C:
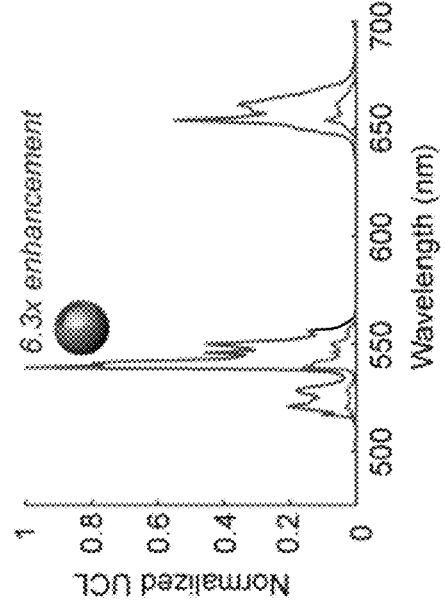
FIGS. 2A-2C show upconversion luminescence spectra and lifetime. (2A) Ensemble upconversion luminescence spectra of $NaY_{0.78}F_4:Yb_{0.2}Er_{0.02}$ and $NaY_{0.78}F_4:Yb_{0.2}Er_{0.02}@ NaYF_4$ using 980 nm excitation at 20 W cm$^{-2}$. (2B) Upconversion luminescence spectra of $NaYF_4@NaYb_{0.98}F_4$: $Er_{0.02}$ and $NaYF_4@NaYb_{0.98}F_4$: $Er_{0.02}@NaYF_4$. (2C) Upconversion luminescence decay of $NaYF_4@NaYb_{1-x}F_4$: $Er_x@NaYF_4$ (x=0.02, 0.04, 0.08, 0.16) at 541 nm, according to the current invention.
Figure 2B:
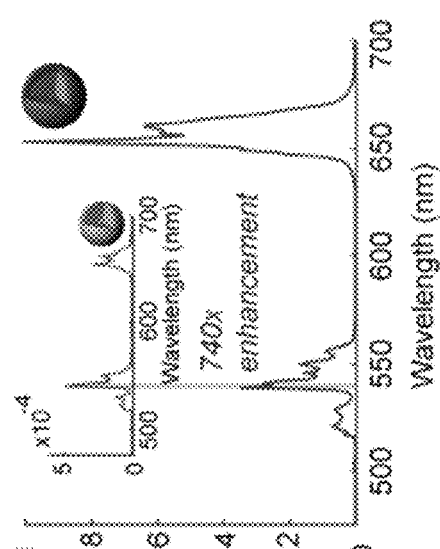
Figure 2A:
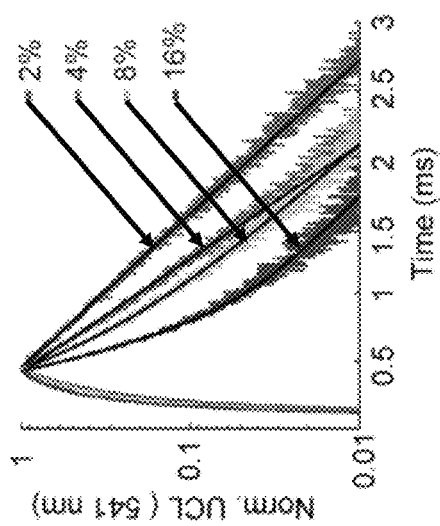

FIG. 2A shows a representative ensemble upconversion luminescence spectrum with 980 nm laser excitation of a solution containing 22 nm NaY$_{0.78}$F$_4$:Yb$_{0.2}$Er$_{0.02}$ UCNPs. Emission peaks centered at 520 nm, 541 nm, and 654 nm (FIGS. 2A-2B) are attributed to the transitions from the $^2H_{11/2}$, $^4S_{3/2}$, and $^4F_{9/2}$ excited states to the $^4I_{15/2}$ ground state, respectively. After growing a ~3 nm inert shell on these UCNPs, the upconversion luminescence increased by 6.3 times while the spectrum remained unchanged (FIG. 2A). On the other hand, when an inert shell was added to NaYF$_4$@NaYb$_{0.98}$F$_4$:Er$_{0.02}$ to form the core-shell-shell structure, an extraordinary 740-fold green emission enhancement was observed (FIG. 2B). However, the seemingly more effective shell for NaYbF$_4$ could be due to more significant energy migration to the surface quenching sites with high Yb$^{3+}$ content.

The luminescence lifetimes were examined as they are usually correlated with the particle brightness (FIG. 2C and Table 1). Interestingly, the lifetime of NaYF$_4$@NaYb$_{0.98}$F$_4$:Er$_{0.02}$ (22.6 nm) is shorter than that of NaY$_{0.78}$F$_4$:Yb$_{0.2}$Er$_{0.02}$ (22.0 nm), suggesting that high level Yb$^{3+}$ induced concentration quenching. However, similar lifetimes were observed when both types of particles were coated with an inert shell, implying that quenching at high level Yb$^{3+}$ is predominantly due to energy migration to the surface defects rather than self-quenching among Yb$^{3+}$ ions. Concentration quenching was also found with increasing Er$^{3+}$ content, which was exhibited as a reduced lifetime (FIG. 2C and Table 1). This result presents a trade-off between concentration quenching and luminescence enhancement with higher activator content. The optimal Er$^{3+}$ concentration for maximizing the brightness per unit volume in NaYF$_4$@NaYb$_{1-x}$F$_4$:Er$_x$@NaYF$_4$ UCNPs requires a comparison at the single-particle level because a precise determination of the UCNPs concentration in solution is nontrivial and could be easily biased by particle aggregation and precipitation. Also, a dense aggregation of particles could lead to partial shielding of surface quenching mechanisms.

TABLE 1

Upconversion lifetime of NaY$_{0.78}$F$_4$:Yb$_{0.2}$Er$_{0.02}$
(22 nm; 27 nm; 33 nm), NaY$_{1-0.2-x}$F$_4$:Yb$_{0.2}$Er$_x$
(x = 0.04, 0.08, 0.16), core-shell NaY$_{0.78}$F$_4$:Yb$_{0.2}$Er$_{0.02}$@NaYF$_4$, NaYF$_4$@NaYb$_{0.98}$F$_4$:Er$_{0.02}$,
and NaYF$_4$@NaYb$_{1-x}$F$_4$:Er$_x$@NaYF$_4$,
(x = 0.02, 0.04, 0.08, 0.16, 0.50).

| Samples | Lifetime (541 nm, microsec) | Lifetime (654 nm, microsec) |
|---|---|---|
| NaY$_{0.78}$F$_4$:Yb$_{0.2}$Er$_{0.02}$ | 113 | 227 |
| NaY$_{0.78}$F$_4$:Yb$_{0.2}$Er$_{0.02}$ 27 nm | 117 | 232 |
| NaY$_{0.78}$F$_4$:Yb$_{0.2}$Er$_{0.02}$ 33 nm | 123 | 305 |
| NaY$_{0.78}$F$_4$:Yb$_{0.2}$Er$_{0.02}$@NaYF$_4$ | 490 | 483 |
| NaY$_{0.76}$F$_4$:Yb$_{0.2}$Er$_{0.04}$ | 74 | 184 |
| NaY$_{0.72}$F$_4$:Yb$_{0.2}$Er$_{0.08}$ | 68 | 178 |
| NaY$_{0.64}$F$_4$:Yb$_{0.2}$Er$_{0.16}$ | 66 | 174 |
| NaYF$_4$@NaYb$_{0.98}$F$_4$:Er$_{0.02}$@NaYF$_4$ | 493 | 423 |

TABLE 1-continued

Upconversion lifetime of $NaY_{0.78}F_4:Yb_{0.2}Er_{0.02}$
(22 nm; 27 nm; 33 nm), $NaY_{1-0.2-x}F_4:Yb_{0.2}Er_x$
(x = 0.04, 0.08, 0.16), core-shell $NaY_{0.78}F_4:Yb_{0.2}Er_{0.02}@$
$NaYF_4$, $NaYF_4@NaYb_{0.98}F_4:Er_{0.02}$,
and $NaYF_4@NaYb_{1-x}F_4:Er_x@NaYF_4$,
(x = 0.02, 0.04, 0.08, 0.16, 0.50).

| Samples | Lifetime (541 nm, microsec) | Lifetime (654 nm, microsec) |
|---|---|---|
| $NaYF_4@NaYb_{0.96}F_4:Er_{0.04}@NaYF_4$ | 361 | 329 |
| $NaYF_4@NaYb_{0.92}F_4:Er_{0.08}@NaYF_4$ | 351 | 304 |
| $NaYF_4@NaYb_{0.84}F_4:Er_{0.16}@NaYF_4$ | 267 | 286 |
| $NaYF_4@NaYb_{0.50}F_4:Er_{0.50}@NaYF_4$ | 190 | 237 |
| $NaYF_4@NaYb_{0.98}F_4:Er_{0.02}$ | 85 | 209 |

To characterize the optical properties of single nanoparticles, the UCNPs in cyclohexane (400 ng/ml) were drop-cast onto a gridded coverslip with alphanumerically labeled photoetched squares for correlative luminescence and SEM (FIG. 3A, FIG. 18). After correcting the wide-field fluorescence images by the laser illumination profile, the diffraction-limited fluorescent spots were carefully registered to corresponding positions on electron micrographs and each spot was examined at 200,000× magnification that is sufficient to clearly resolve and verify the size of the individual nanoparticles. The 8% Er-doped core-shell-shell UCNPs and the canonical 22.0 nm core-only $NaY_{0.78}F_4:Yb_{0.2}Er_{0.02}$ (FIG. 3a) were first compared, which have the same optically active volume of ~22 nm. At a moderate power density of 625 W cm$^{-2}$ (a typical wide-field microscope uses 1-10 kW cm$^{-2}$), the 8% Er CSS UCNPs emits ~20,000 photons per second (pps, obtained from the integrated volume of the 2D Gaussian fit), which is 5 times brighter than the standard core-only UCNPs (FIG. 3B).

Figure 14B:
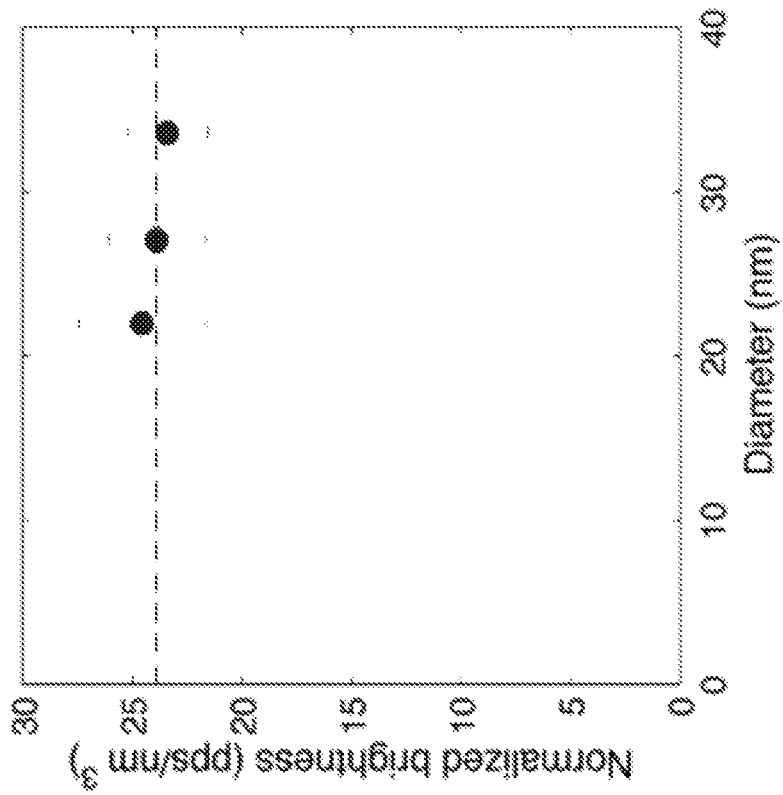
Figure 14A:
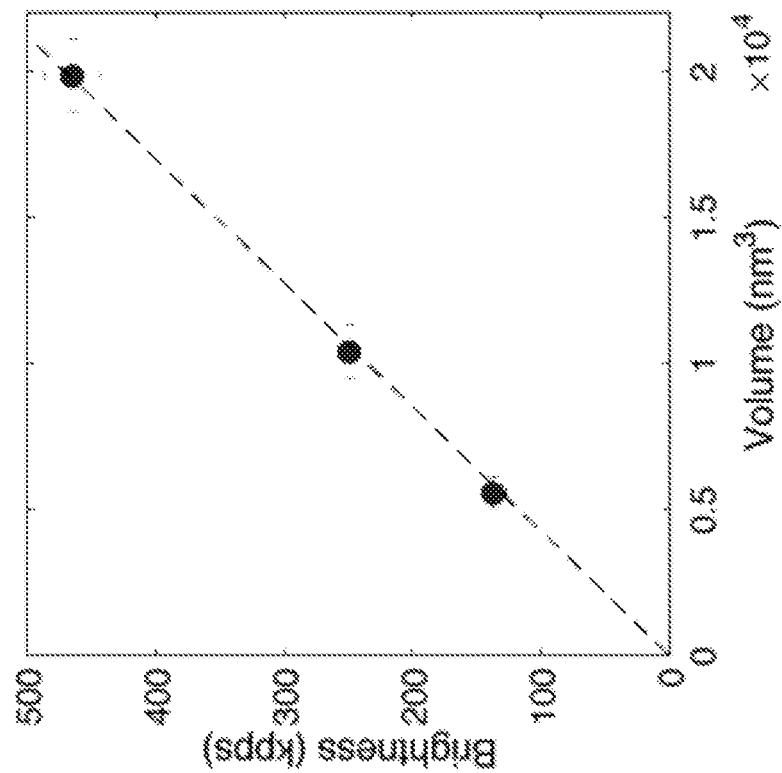

When the power density was further lowered to 8 W cm$^{-2}$, the core-shell-shell UCNPs are drastically brighter than the standard core-only UCNPs by a factor of 150 (FIG. 3A-3B), demonstrating single-particle imaging of sub-30 nm UCNPs at a power that is about five orders of magnitude smaller than what was previously used. Reliable single-particle detection requires a minimum signal to noise ratio (SNR) of ~5. To achieve SNR of 5 at 8 W cm$^{-2}$, at least 15-sec long exposure was needed for the standard core-only UCNPs, while it took only 100 milliseconds for the core-shell-shell UCNPs. It is worth noting that most live whole animal imaging is performed with ~100 mW cm$^{-2}$. At these lower intensities, the core-shell-shell UCNPs are estimated to be ~5000-fold brighter than the core-only UCNPs (FIGS. 14A-14B), which will significantly improve the overall detectability and reduce nanoparticle dosage. Imaging single particles at <100 mW cm$^{-2}$ may employ pulsed excitation with high peak intensity and at low duty cycle to keep the average power low enough for in vivo experiments.

Figure 11:
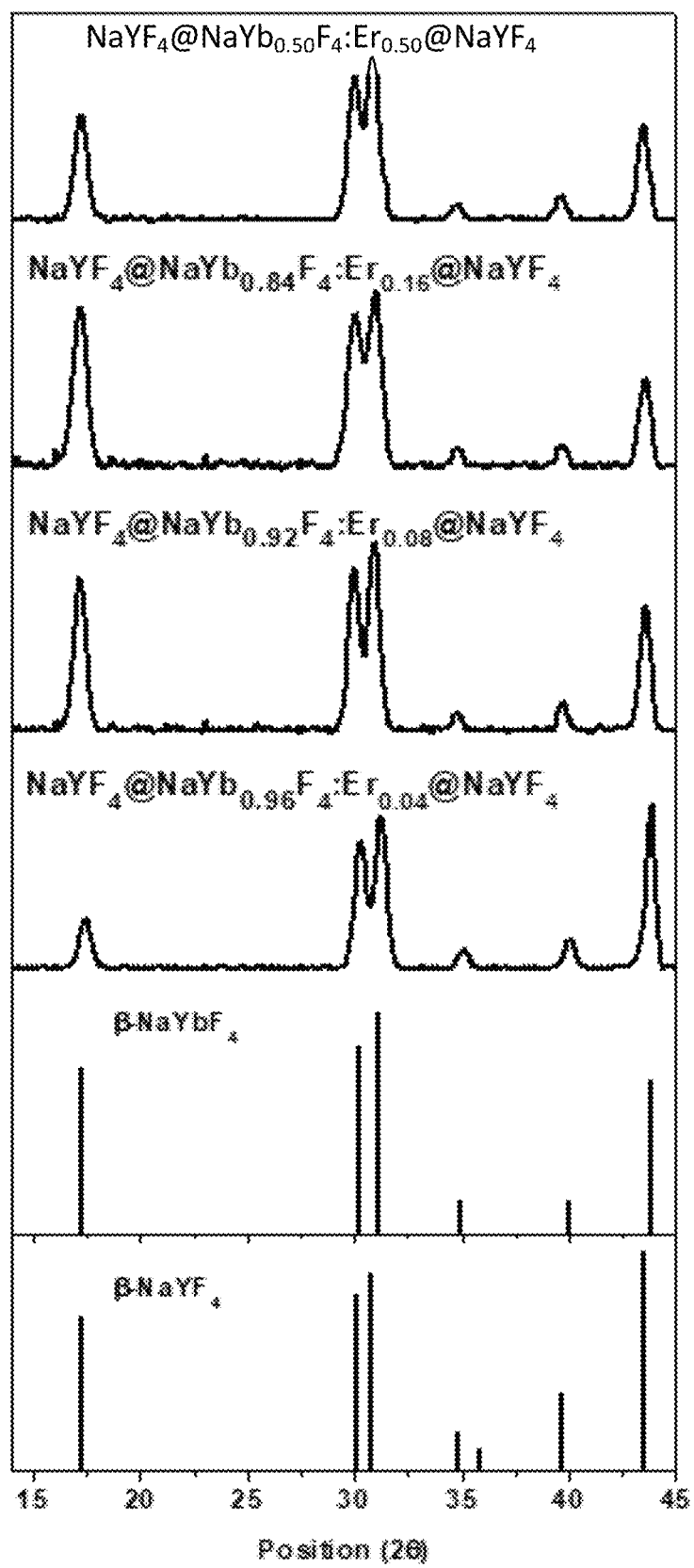
FIG. 11 shows XRD of NaYF$_4$@NaYb$_{1-x}$F$_4$:Er$_x$@NaYF$_4$, (x=0.04, 0.08, 0.50), and standard hexagonal phase NaYF$_4$ and NaYbF$_4$, according to the current invention.
Figure 12:
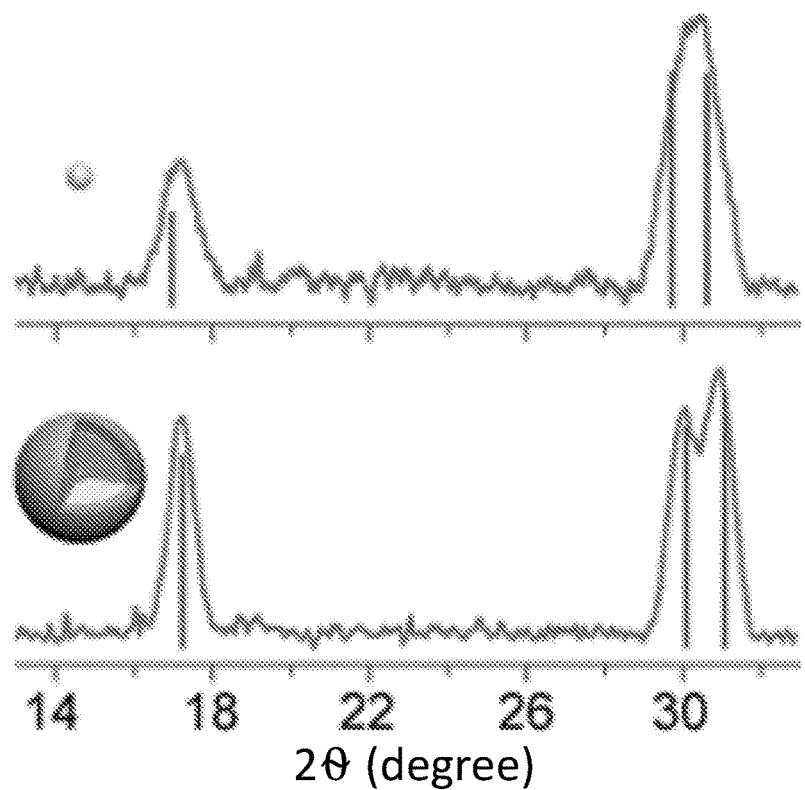
FIG. 12 shows XRD of seed NaYF$_4$ and core-shell-shell NaYF$_4$@NaYb$_{0.98}$F$_4$:Er$_{0.02}$@NaYF$_4$. Vertical lines correspond to the reference data for standard hexagonal phase NaYF$_4$ (top) and NaYbF$_4$ (bottom), according to the current invention.

To further investigate the heterogeneity of single-particle luminescence, measurements on hundreds of individual nanoparticles were used to assemble brightness histograms (FIG. 3G, and FIGS. 15A-15B). For each type of UCNPs, about 20 field of views (FOVs) were rapidly recorded using wide-field illumination and an EMCCD camera. FIGS. 3C-3F show representative luminescence images measured at 625 W cm$^2$ for 4 different UCNPs: 22.0 nm (FIG. 3C) and 27.1 nm (FIG. 3D) core-only $NaY_{0.78}F_4:Yb_{0.2}Er_{0.02}$, 29.1 nm core-shell $NaY_{0.78}F_4:Yb_{0.2}Er_{0.02}@NaYF_4$ (FIG. 3E), and 29.4 nm core-shell-shell $NaYF_4@NaYb_{0.92}F_4:Er_{0.08}@NaYF_4$ (FIG. 3F). Each histogram contains a main Gaussian peak, representing the upconversion luminescence distribution of the single particles. Most of the diffraction-limited fluorescent spots were confirmed by the luminescence/SEM co-localization data to be individual UCNPs, with occasional appearance of dimers or small oligomers (FIG. 16). The histograms generated showed that the fractional number of oligomers (the number of particles with brightness above the monomer brightness distribution) vary between 0.3% and 13%. The core-shell-shell structure is the brightest among the four types of UCNPs, but also with wider distribution. If the measured brightness distribution is solely due to the nanoparticle volume distribution, one would only expect a ~12% distribution. Considering different sources of variation add in quadrature, the measured ~21% luminescence distribution indicates a ~17% heterogeneity due to factors other than nanoparticle size (FIG. 8, FIG. 9, and FIG. 11), which could include doping inhomogeneity and crystal defects in the more complicated three-step core-shell-shell synthesis.

Figure 4:
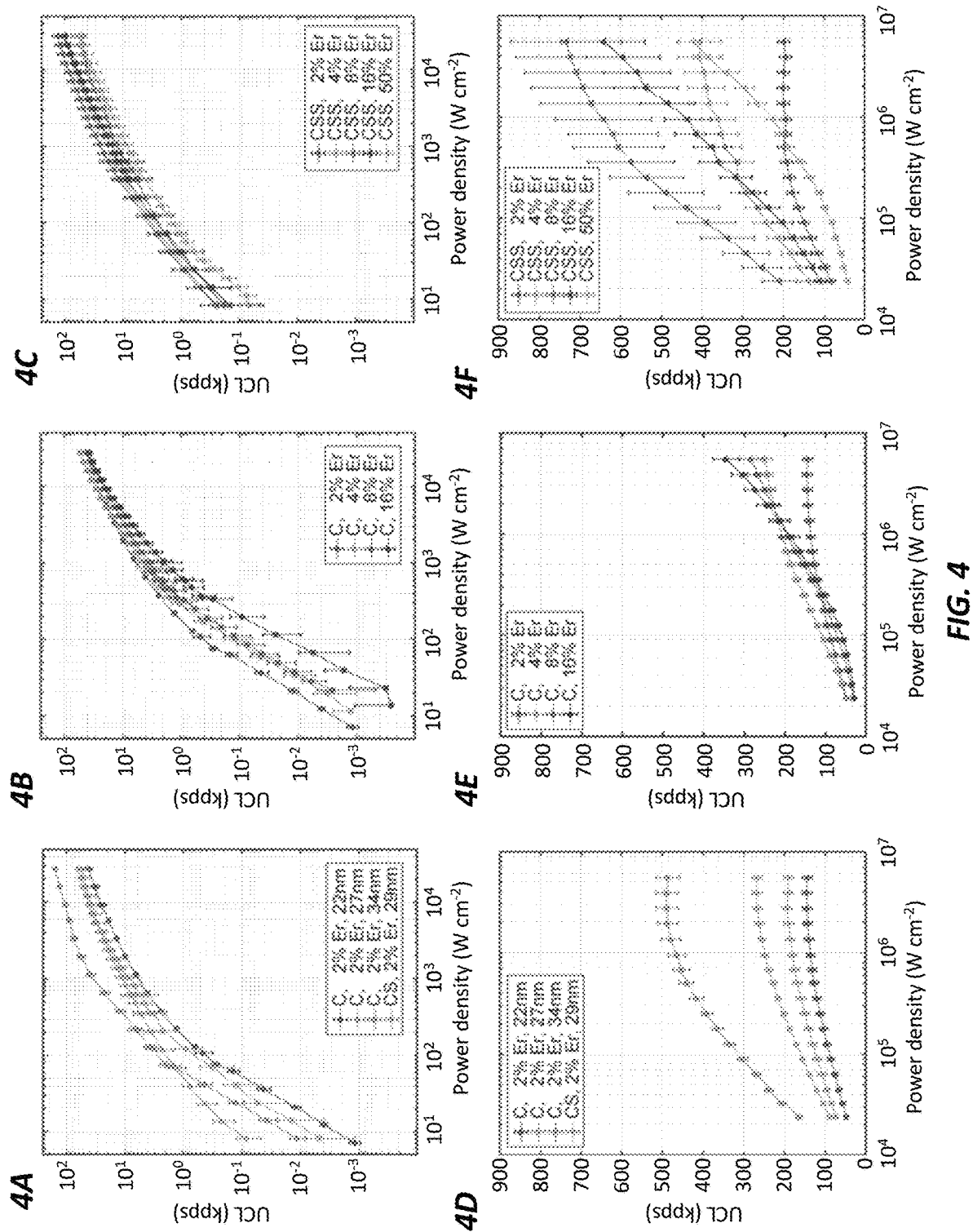
FIGS. 4A-4F show single-particle saturation curves. (4A-4C) Saturation curves at power densities from 8 W cm$^{-2}$ to 27 kW cm$^{-2}$ obtained with wide-field microscopy. All types of particles excluding the 27 nm and 33 nm core-only have the same ~22 nm active volume. The kink in the saturation curves under low power densities is due to the addition of an OD2 ND filter. (4D-4F) Saturation curves at power densities from 20 kW cm$^{-2}$ to 6 MW cm$^{-2}$ obtained with confocal microscopy (see FIGS. 17A-17E for confocal images). (4A, 4D) compares UCL for different sizes of core-only UCNPs (2% Er) and a 29 nm core-shell UCNPs grown from the 22 nm core. (4B, 4E) compares UCL for core-only UCNPs (22 nm) with different Er$^{3+}$ doping. (4C, 4F) compares UCL for core-shell-shell UCNPs with different Er$^{3+}$ doping. Notice that log-scale is used for the y-axis in (4A-4C) while linear-scale is used in (4D-4F), according to the current invention.

In order to systematically compare the brightness of the core-shell-shell structure to other UCNPs designed to enhance upconversion luminescence, the power-dependent luminescence curves (aka "saturation curves") were measured for single particles across nearly 6 orders of magnitudes in power density: ~8 W cm$^{-2}$ to ~6 MW cm$^{-2}$ (FIG. 4). Each saturation curve was obtained by averaging over at least 30 single particles within an FOV. The 8% Er-doped CSS UCNPs were found to be the brightest among all 12 types of UCNPs studied in this work across all power densities, and most importantly even brighter than the larger 33.6 nm core-only $NaY_{0.78}F_4:Yb_{0.2}Er_{0.02}$, by a factor of 21 at 8 W cm$^{-2}$. FIG. 4A and FIG. 4C compare the saturation curves for the core-only $NaY_{0.78}F_4:Yb_{0.2}Er_{0.02}$ with three different sizes (22.0 nm, 27.1 nm, and 33.6 nm), as well as the core-shell structure synthesized based on the 22.0 nm core. The emission intensities of the three core-only UCNPs scale linearly with particle volume (FIG. 4A, FIGS. 17A-17E and FIG. 18), indicating that good crystal quality was maintained for these particles as the larger particles were epitaxially grown from the smaller particles.

The core-shell UCNPs are brighter than its precursor 22 nm core-only nanoparticles (FIG. 4A), especially at intensities <kW cm$^{-2}$ (50-fold enhancement at 8 W cm$^{-2}$). However, the enhancement dropped to only ~1.5 above 10 kW cm$^{-2}$, and based on volume-normalized emission, the 22 nm core-only UCNPs are actually brighter than the 29 nm core-shell UCNPs at intensities >2 kW cm$^{-2}$ (FIG. 16). This illustrates that the inert shell is effective in preventing luminescence quenching at low power, but the extra shell thickness becomes an overhead at higher irradiance where quenching of the core-only UCNPs is not as severe. This power-dependent luminescence enhancement of the core-shell structure could explain the one or two orders of magnitude higher enhancement factor obtained from the ensemble measurement compared to previous single-particle experiments, as ensemble measurement typically uses tens of W cm$^{-2}$ while single-particle characterization with confocal microscopy employs >10 kW cm$^{-2}$. More importantly, the inert shell in the core-shell-shell structure has greater luminescence enhancement—several hundred-fold at low power density and 4.4-fold at high power density. At the lower power density ranging from ~ 8 W cm$^{-2}$ to ~ 75 W cm$^{-2}$, the luminescence of the core-only UCNPs exhibit a typical quadrature power dependence ($I \propto P^2$), consistent with a two-photon upconversion process (FIG. 4A and FIG. 4B). In contrast, when an inert shell is incorporated in the core-shell and core-shell-shell structure, a shallower slope of ~1.2 was observed for their saturation curves. This behavior suggests that these UCNPs are in an effectively higher power limit where the depopulation of the $Yb^{3+}$ excited state is slowed down due to reduced relaxation pathways to surface quenching sites.

FIG. 4B and FIG. 4E show the effect of $Er^{3+}$ concentration on upconversion emission. As the $Er^{3+}$ content increases from 2% to 16% in the core-only $NaY_{1-0.2-x}F_4:Yb_{0.2}Er_x$, the luminescence drops significantly at low power densities (FIG. 4B). In contrast, the trend reverses at >200 kW cm$^{-2}$ (FIG. 4E). This concentration quenching has been observed in both ensemble and single-particle measurements and agrees well with reported simulations. However, such concentration quenching is not so apparent in the core-shell-shell structure under low irradiance (FIG. 4C) where the luminescence of the 2%-16% $Er^{3+}$-doped core-shell-shell UCNPs is within a factor of 2 at 8 W cm$^{-2}$. This result again highlights the effectiveness of the inert shell in decreasing concentration-dependent quenching. At significantly higher $Er^{3+}$ doping of 50% in the core-shell-shell structure, the upconversion emission dropped by a factor of 3.5 compared to the 8% doped UCNPs. At higher power densities above 100 kW cm$^{-2}$, the brightness of the five core-shell-shell UCNPs start to diverge (FIG. 4F), with a trend that is similar to the core-only UCNPs with varying $Er_3+$ doping. Nevertheless, the 8% $Er^{3+}$-doped core-shell-shell remains the brightest formulation tested in this power density region.

To put these single-particle measurements into perspective of other fluorescent probes, the upconversion quantum yield (UCQY) has been measured under 980 nm laser excitation at 120 W cm$^{-2}$ (Table 2). Consistent with the literature, the UCQY for the core-only UCNPs is low and simply increasing the particles size did not provide much improvement, with 0.10±0.04% and 0.15±0.05% for the 22 nm and 34 nm UCNPs, respectively. In contrast, UCQY was greatly increased to 5.03±0.60% for the 29 nm core-shell structure due to reduced surface quenching. The brightest single-particle probe presented herein, the core-shell-shell $NaYF_4@NaYb_{0.92}F_4:Er_{0.08}@NaYF_4$, was found to have a similar UCQY (5.42±0.45%). However, UCQY is calculated as the number of photons emitted divided by the number of photons absorbed. The core-shell-shell UCNPs of the current invention was designed with 92% $Yb^{3+}$ to significantly increase 980 nm absorption, and therefore, even higher emission rates may not be exhibited as higher UCQY. This illustrates the important fact that even though UCQY reflects the amount of upconversion to a certain extent, the figure of merit in single-particle imaging should be the emission rates at given illumination intensity.

TABLE 2

The summary of upconversion quantum yield.

| | Upconversion quantum yield |
|---|---|
| Core, 2% Er, 22 nm | 0.10% ± 0.04% |
| Core, 2% Er, 33 nm | 0.15% ± 0.05% |
| Core-shell, 2% Er, 29 nm | 5.03% ± 0.60% |
| Core-shell-shell, 8% Er, 29 nm | 5.42% ± 0.45% |

Various strategies designed to optimize the brightness of single UCNPs have been systematically investigated and benchmarked herein. Various formulations and sizes of $Er^{3+}$-doped UCNPs across ~6 orders of magnitude in power density were tested. The luminescence brightness per unit volume of these particles is significantly increased by a core-shell-shell structure: a 6 nm diameter $NaYF_4$ core, an epitaxial shell of $NaYbF_4$ with x % $Er^{3+}$ substitution of $Yb^{3+}$, followed by a 3 nm thick $NaYF_4$ shell. In the parameter space studied, x=8% gives the best results. At an intensity of 8 W cm$^{-2}$, a 150-fold enhancement over the commonly used formulation of $NaY_{0.78}F_4:Yb_{0.2}Er_{0.02}$ is observed. This development opens up the possibility of photostable single-molecule tracking at very low irradiance, and even greater comparative sensitivity for cell identification and tracking in live animals.

Additionally, complex behavior of single-particle brightness as a function of illumination power density was revealed, and resolves some of the seemingly contradictory enhancement factors or quantum yields in the literature. Specifically, it is shown why low power ensemble measurements cannot be directly compared to high power single nanoparticle measurements. Furthermore, the current invention demonstrates the value of quantitative and systematic characterization of laser power-dependent UCNPs brightness with well-calibrated absolute power density measurements. To this end, a methodology was developed that allows such unambiguous measurements at the single-particle level that provides a reliable experimental platform for continuing efforts in optimizing UCNPs tailored for various applications.

Turning now to an exemplary synthesis of 22 nm $NaY_{0.78}F_4:Yb_{0.2}Er_{0.02}$. To a 100 mL three-necked flask, 6 mL oleic acid (OA) and 15 mL 1-octadecene (ODE) were added given amounts of $YCl_3.6H_2O$ (0.78 mmol), $YbCl_3.6H_2O$ (0.20 mmol) and $ErCl_3.6H_2O$ (0.02 mmol). The mixture was heated to 160° C. to form a clear solution, cooled down to room temperature and 10 mL of methanol solution containing NaOH (2.5 mmol) and $NH_4F$ (4 mmol) were added. The mixture was stirred for 30 min at room temperature, then heated to 120° C. and kept for another 30 min. Subsequently, the solution was heated to 300° C. and maintained for 1 h in an argon atmosphere. After the solution was cooled naturally, 25 mL ethanol was added, and the resulting mixture was centrifugally separated (12000 rpm for 10 min) to a compact pellet, and the supernatant was discarded. The products were collected and washed with cyclohexane and ethanol (40 mL, 1:1, v/v) three times. The UCNPs (diameter 22.0 nm±0.7 nm) was stored in 8 mL cyclohexane.

For an exemplary synthesis of 29 nm core-shell $NaY_{0.78}F_4:Yb_{0.2}Er_{0.02}@NaYF_4$ and 27 nm $NaY_{0.78}F_4:Yb_{0.2}Er_{0.02}$, to a 100 mL three-necked flask, 3 mL oleic acid (OA) and 8 mL 1-octadecene (ODE) were added given amounts of $YCl_3.6H_2O$ (0.40 mmol) for the core-shell $NaY_{0.78}F_4:Yb_{0.2}Er_{0.02}@NaYF_4$ synthesis and $RECl_3$ (0.30 mmol, 78% $Y^{3+}$, 20% $Yb^{3+}$, 2% $Er^{3+}$) for the 27 nm $NaY_{0.78}F_4:Yb_{0.2}Er_{0.02}$ synthesis. The mixture was heated to 160° C. to form a clear solution under argon atmosphere. After cooling to room temperature, half volume (4 mL) of the previously prepared 22 nm $NaY_{0.78}F_4:Yb_{0.2}Er_{0.02}$ UCNPs in cyclohexane and 5 mL methanol solution containing 1 mmol NaOH and 1.5 mmol $NH_4F$ were added into the reaction flask and stirred for 30 min. The solution was heated to remove low-boiling solvent, kept at 120° C. for 30 min, and then heated to 300° C. and maintained for 1 h under argon atmosphere. The subsequent purification steps are the same as used for 22 nm $NaY_{0.78}F_4:Yb_{0.2}Er_{0.02}$ UCNPs described above. The final particle diameter was 29.1 nm±1.0 nm for the core-shell $NaY_{0.78}F_4:Yb_{0.2}Er_{0.02}@NaYF_4$ and 27.1±0.8 for 27 nm $NaY_{0.78}F_4:Yb_{0.2}Er_{0.02}$ UCNPs.

For an exemplary synthesis of 33 nm $NaY_{0.78}F_4:Yb_{0.2}Er_{0.02}$, the 33 nm core-only UCNP was obtained by growing another layer on 27 nm $NaY_{0.78}F_4:Yb_{0.2}Er_{0.02}$ UCNP. The procedure is the same as for synthesizing 27 nm $NaY_{0.78}F_4$:$Yb_{0.2}Er_{0.02}$. The final particle diameter was 33.6 nm±0.7 nm.

Regarding an exemplary synthesis of $NaY_{1-0.2-x}F_4$: $Yb_{0.2}Er_x$ (x=0.04, 0.08, 0.16): the procedure is the same as for 22 nm $NaY_{0.78}F_4$:$Yb_{0.2}Er_{0.02}$, except with varying the $Er^{3+}$ concentration while keeping the $Yb^{3+}$ concentration at 20%. The final particle diameter was 22.4 nm±0.8 nm, 20.8 nm±0.8 nm, and 21.5 nm±0.6 nm, respectively.

For Synthesis of an exemplary 6.0 nm p-$NaYF_4$ seed, 1.0 mmol $YCl_3.6H_2O$ aqueous solution was added into the mixture of 10 mL oleic acid and 10 mL octadecene, then the mixture was heated to 160° C. and kept for 30 min to remove water. The solution is cooled to <50° C., and 0.34 g $NH_4F$ and 2.03 g sodium oleate were quickly added into the reaction. The solution was heated to 120° C. and kept for 30 min, and then heated to 300° C. and maintained for 30 min at argon atmosphere. The subsequent purification steps are the same as used for 22 nm $NaY_{0.78}F_4$:$Yb_{0.2}Er_{0.02}$ UCNPs. The product was stored in 20 mL cyclohexane. The final particle diameter was 6.0 nm±0.6 nm.

Regarding an exemplary synthesis of $NaYF_4$@$NaYb_{1-x}F_4$:$Er_x$, 0.40 mmol $RECl_3.6H_2O$ (98% $Yb^{3+}$, 2% $Er^{3+}$; 96% $Yb^{3+}$, 4% $Er^{3+}$; 92% $Yb^{3+}$, 8% $Er^{3+}$; 84% $Yb^{3+}$, 16% $Er^{3+}$; or 50% $Yb^{3+}$, 50% $Er^{3+}$) was added into 3 mL oleic acid and 8 mL octadecene in a 100 mL three-neck flask. The solution was heated to 160° C. to form a clear solution under argon atmosphere. After the mixture was cooled to room temperature, 2 mL of the prepared 6.0 nm β-$NaYF_4$ seed in cyclohexane and 5 mL methanol solution containing 1 mmol NaOH and 1.5 mmol $NH_4F$ were added into the reaction flask and stirred for 30 min. The solution was heated to 120° C. to remove low-boiling solvents for 30 min, and then heated to 300° C. and maintained for 1 h under argon atmosphere. The subsequent purification steps are the same as used for 22 nm $NaY_{0.78}F_4$:$Yb_{0.2}Er_{0.02}$. The product was stored in 8 mL cyclohexane.

For and exemplary synthesis of $NaYF_4$@$NaYb_{1-x}F_4$: $Er_x$@$NaYF_4$ (x=0.02, 0.04, 0.08, 0.16, 0.50), the procedure is the same with that of core-shell $NaY_{0.78}F_4$: $Yb_{0.2}Er_{0.02}$@$NaYF_4$, except using the prepared $NaYF_4$@$NaYb_{1-x}F_4$: $Er_x$ (x=0.02, 0.04, 0.08, 0.16, 0.50) to replace 22 nm $NaY_{0.78}F_4$:$Yb_{0.2}Er_{0.02}$. The final particle diameter was 28.3 nm±1.6 nm, 28.2 nm±2.1 nm, 29.4 nm±1.2 nm, 27.9 nm±2.0 nm, and 28.4 nm±1.8 nm, respectively. The product was stored in 8 mL cyclohexane.

Turning now to characterization, X-ray diffraction (XRD) measurements were performed on a Bruker Single Crystal Diffracometer D8 Venture (Cu Kα radiation, λ=1.54056 Å). The size and morphology of UCNP were determined at 100 kV using a JEOL JEM-1400 TEM. STEM and high-resolution TEM imaging were carried out in a FEI Tecnai G2 F20 X-TWIN TEM. The prepared samples were dispersed in cyclohexane and dropped onto the surface of a copper grid for TEM analysis. The upconversion luminescence emission spectra were recorded on an Edinburgh LFS-920 instrument, but the excitation source using an external 0-1 W adjustable 980 nm semiconductor laser (Beijing Hi-Tech Optoelectronic Co., China) with an optic fiber accessory, instead of the Xeon source in the spectrophotometer. Upconversion luminescence lifetime was measured with a phosphorescence lifetime spectrometer (FSP920-C, Edinburgh) equipped with a tunable mid-band OPO pulse laser as excitation source (410-2400 nm, 10 Hz, pulse width ≤5 ns, Vibrant 35511, OPOTEK). All the photoluminescence studies were carried out at room temperature.

Regarding Upconversion quantum yield, quantum yield measurements were performed as described in literature. Luminescence spectrometer (Edinburgh Instruments LFSP920) was modified with NIR PMT (HAMAMATSU, C9940-02, No. CA0142) as the new detector for detecting the 980 nm CW excitation light. An integrating sphere was used for measuring the quantum yield. An excitation power density of 120 W cm$^{-2}$ was used for all the measurements. Un-doped $NaYF_4$ was used as a reference sample. The upconversion quantum yield was calculated according to the following equation where UCQY is the quantum yield, $I_{em,sample}$ and $I_{em,reference}$ are the integrated emission intensities (500 nm to 700 nm) from the sample and the reference (close to zero), respectively. $I_{ex,reference}$ and $I_{ex,sample}$ are the integrated intensities (970 nm to 990 nm) of the excitation light in the presence of the reference and the sample, respectively.

$$UCQY = \frac{\text{visible photons emitted}}{\text{980 nm photons absorbed}} = \frac{I_{em,sample} - I_{em,reference}}{I_{ex,reference} - I_{ex,sample}}$$

Since the absorption of 980 nm by UCNPs is very small compared to the total excitation intensity, an OD4 980 nm attenuation filter (Giai Photonics Co., Ltd.) was placed in front of NIR PMT to prevent saturation of the detector.

With respect to sample preparation for optical characterization, for both wide field and confocal microscopy, high NA oil objectives were used. Approximately 400 ng/ml nanoparticles in cyclohexane were dropcast onto a clean and dry No 1.5 cover glass briefly pre-coated with 1% (w/v) poly-lysine. Excess nanoparticles were rinsed off with cyclohexane. The cover glass is attached to a standard microscope slide using double-sided tape for a rigid mounting.

Using wide field imaging, single-particle optical characterization under low to moderate illumination was done using a lab constructed microscope system equipped with wide field epi-illumination of a 976 nm fiber laser through a Nikon 100× NA 1.49 Oil objective. The upconverting luminescence signal was recorded on a Andor iXon 897 EMCCD. Custom IDL code was used to identify individual nanoparticles and perform 2D Gaussian fit to localize the particle and deduce the emission rate from the fitted amplitude.

Confocal microscopy was used for moderate to high excitation power density, where single-particle optical characterization was performed on a home-built stage scanning confocal microscope with a Nikon 60× NA 1.49 oil objective and a 976 nm fiber laser. A data acquisition code written in Matlab controls the laser power output, and scans the sample mounted on a high precision piezo-electric stage (Madcity Labs Nano LP-200. Photoluminescence was recorded on an avalanche photodiode (Excelitas SPCM-AQRH-12).

Turning now to illumination profile correction and power density calibration, the power density of excitation S were experimentally determined using the following equation, $$S(r) = Se^{\frac{r^2}{2\sigma_{ex}^2}} = \frac{P_{obj}}{2\pi\sigma_{ex}^2} e^{-\frac{r^2}{2\sigma_{ex}^2}},$$

where $P_{obj}$ is the measured 976 nm laser power out of the objective lens (using a Thorlabs PM100D power meter placed directly onto the surface of the microscope objective), and $\sigma_{ex}$ is the size of the illumination profile at the sample plane. The width of the point spread function was measured by stepping the translation stage in 78 nm step size. The $\sigma_{ex}$ width is approximated by fitting either the confocal point spread function or the normalized wide field illumination profile $\tilde{S}(x,y)$ into a 2D Gaussian.

The wide-field illumination profile is computed from a position-dependent luminescence profile $\tilde{I}(x,y)$ (photons detected "counts" per captured camera frame) of a single UCNP $$\tilde{I}(x,y) \equiv \frac{l(x,y)}{l_{max}} = \tilde{S}(x,y)^\alpha,$$

where $\tilde{I}(x,y)$ is reconstructed from a single UCNP by scanning the sample stage across the field of view (FOV) with equal step size of 1 μm and α is estimated from the local slope of a measured saturation curve (FIG. 4).

In order to build reliable single-particle luminescence statistics, we always perform illumination profile correction $I_{cor}(x,y)$ from the wide-field image data $I_{raw}(x,y)$:

$$I_{cor}(x,y) = \frac{I_{raw}(x,y)}{\tilde{I}(x,y)} = \frac{I_{raw}(x,y)}{l(x,y)} l_{max}$$

For the Rose criterion and single-molecule visibility, the minimum exposure time using the Rose criterion which imposes a threshold signal to noise ratio (SNR) k~5 on[1,2]. The SNR was calculate with integrated signal instead of per pixel based peak intensity. Consider a single particle at location $(x_0, y_0)$ with detected luminescence $I(x,y)$ (units of photons/pixel/camera frame) approximated by a 2D Gaussian $$I(x,y) = \frac{I_0}{2\pi\sigma^2} e^{-\frac{(x-x_0)^2 + (y-y_0)^2}{2\sigma^2}},$$

where fitted amplitude $I_0$ is just particle emission rate $j$ multiply by exposure time $t$. Assuming a time dependent background current $b^2$ (photons/pixel-sec) and a readout noise $n$ (fluctuations in the digitized signal with no photons detected, in units of counts) are given, the Rose criterion gives $$SNR = \frac{jt}{\sqrt{jt + 4\pi\sigma^2(b^2 t + n^2)}} \geq k.$$

The corresponding minimum exposure time is $$t_{SNR} = \frac{k^2}{j}\left(1 + \frac{4\pi\sigma^2 b^2}{j}\right) \frac{1 + \sqrt{1 + \frac{16\pi\sigma^2 j^2 n^2}{k^2(j + 4\pi\sigma^2 b^2)^2}}}{2} \approx$$

$$\frac{k^2}{j}\left(1 + \frac{4\pi\sigma^2 b^2}{j} + \frac{4\pi\sigma^2 n^2}{k^2}\right)$$

For EMCCD, the readout noise with electron multiplication is less than the equivalent of one electron "count", n<<1. With UCNPs, there is very low background count from light scattering and other fluorescent impurities on the surface, i.e. $b^2 \ll j$. Take a value of σ to be 1.7 pixel and k=5, the minimum exposure time can be approximated as $t_{SNR} \approx 28/j$. This minimum exposure time $t_{SNR}$ gives the lower bound of detecting a nanoparticle with ~90% confidence. For example, at 8 W cm$^{-2}$, it takes only ~100 msec to clearly identify an 8% Er doped core-shell-shell in a single snapshot.

For the Choice of pixel size, better SNR can be achieved by concentrating most of detected photons onto single camera pixel, which results in 2D Gaussian RMS width c to be approaching or even smaller than pixel size a. However, when a narrow PSF is digitized on a pixelated detector array, localization accuracy is deteriorated. The optimal ratio of Gaussian width c to pixel size a, can be estimated following the descriptions presented by Thompson et al[5], $$\left(\frac{\sigma}{a}\right)_{opt} = \sqrt[4]{\frac{jt}{96\pi(b^2 t + n^2)}}.$$

For the 8% Er-doped core-shell-shell UCNPs at 8 W cm$^{-2}$, with an exposure time of 1 sec, the optimal width to pixel ratio is ~1.7, which is what was used in this study. If only 100 msec exposure time is used, the total magnification could be reduced (σ/α~1) to increase SNR and localization accuracy.

Regarding auto-focusing, focus checking and maintaining throughout data acquisition is critical to quantitative luminescence analysis. Sample drifting introduced focus shift can potentially alter recorded luminescence level hence distort the histogram of intensity and the saturation curve as well. A focus check was performed before scanning every FOV by doing a series of z-scan with an adaptive step size of 20~50 nm according to the magnitude of focus drift. The figure of merit (FoM) for focusing was simply the recorded photon counts $L_{xy}$ in confocal measurements when the excitation was dwelt on a specific nanoparticle at location (x,y).

$$F_{FoM}^{confocal} = L_{xy}$$

In wide-field configuration, the image acquired at each z depth $I(x,y)$ was convolved with a median frequency discrete cosine transfer (MFDCT) operator and the sum of the convolution square is taken as the focus measure.

$$O_{MFDCT} = \begin{bmatrix} 1 & 1 & -1 & -1 \\ 1 & 1 & -1 & -1 \\ -1 & -1 & 1 & 1 \\ -1 & -1 & 1 & 1 \end{bmatrix}$$

$$F_{FoM}^{WF} = \sum_{x=1}^{N} \sum_{y=1}^{M} (O_{MFDCT} * I(x,y))^2$$

The optimal focus was determined by fitting the figure of merit versus z curve to a 2$^{nd}$ order polynomial. The stage was then repositioned to the z corresponding to the maximum of the fitted curve.

Regarding correlative SEM and wide field imaging, nanoparticles were drop-casted as described above onto a glass coverglass containing an alphanumerically labeled grid pattern marked in 50 μm increments (IBIDI grid-50, IBIDI, Germany). The sample was characterized under wide-field illumination at various identifiable locations. For consecutive SEM analysis, a thin layer of 2 nm gold-palladium was sputter-coated (Denton Vacuum, USA) onto the same sample to enhance conductivity, and nanoparticles were imaged using a Zeiss Sigma Field Emission Scanning Electron Microscope (Carl Zeiss Microscopy, Germany) and InLens SE (Secondary Electron) detection. The fine grid pattern served as a navigation guide to locate the FOVs which had previously been optically characterized. Once registration was established between geometric patterns of the fluorescent image and electron micrograph, we then zoomed in to verify the oligomeric state and the size of each individual nanoparticles.

In order to create size-tunable UCNPs with high crystal quality, a core-shell-shell synthesis method is provide herein. According to one embodiment, a small diameter (2.0-8.0 nm) $NaREF_4$(RE=Y, Gd, Lu, Yb, Er, Tm, Ho, Pr, Nd, Eu, Tb, Dy, or La) seed crystals are first synthesized that allow epitaxial growth of size-tunable $NaRE_1F_4$: x % $RE_2$ (RE=Y, Gd, Lu, Yb, Er, Tm, Ho, Pr, Nd, Eu, Tb, Dy, or La, x=0-100). The core-shell UCNPs size is tuned by adjusting the amount of seeds used in the second step of the synthesis, and the required amount of seed crystals for a given desired final nanoparticle size remains the same for different doping ratios. This allowed one to precisely control the overall size of core-shell UCNPs ranging from 10 nm to 50 nm. It is important to note that the small and optically inactive seed only accounts for a few percent of the total volume (2% in the case of 6 nm seed and 22 nm core-shell), therefore not sacrificing the brightness of the UCNPs. Finally, it has been well documented that sensitizer or activators can lead to concentration-quenching and hence decreased luminescence. Non-radiative energy loss can be alleviated by growing an epitaxial shell that reduces the resonant energy transfer among sensitizer or emitter to the surface defects and to vibrational modes of the surrounding solvent. For this reason, a final inert $NaREF_4$ (RE=Y, Gd, Lu, or La) shell (thickness of the inert shell is 1.0 nm-25.0 nm) is added.

In a further embodiment, a core-shell-shell structure $NaYF_4@\ NaYbF_4$: x % Er@ $NaYF_4$ is provided, which allowed for the increase in the amount of sensitizer $Yb^{3+}$ and hence enhancing the 980 nm absorption, while maintaining a small nanoparticle size. In this example structure, 6.0 nm $NaYF_4$ was used as seed, followed by epitaxial growth of $NaYbF_4$: x % Er (x=2%, 4%, 8%, 16%, 50%). The size of core-shell $NaYF_4@NaYbF_4$: x % Er nanoparticle is around 22 nm. After addition of an inert shell, the resulting core-shell-shell $NaYF_4@\ NaYbF_4$: x % Er@$NaYF_4$ UCNPs has an overall size of around 28 nm. This newly developed core-shell-shell $NaYF_4@\ NaYbF_4$: 8% Er@ $NaYF_4$ UCNPs exhibited a 150-fold brightness enhancement over canonical $NaYF_4$: 2% Er, 20% Yb at 8 W cm$^{-2}$, enabling single particle imaging at a power density that is at least three orders of magnitude lower than previously reported.

FIG. 18 shows TEM images of 6 nm $NaYF_4$ seeds, 12 nm $NaYF_4@NaY_xYb_{0.96-x}F_4$:$Tm_{0.04}$ and 20 nm $NaYF_4@NaY_xYb_{0.96-x}F_4$:$Tm_{0.04}$ @$NaYF_4$ (x=0, 0.36, 0.66), described below.

The UCNPs size can be tuned by adjusting the amount of the used 6 nm $NaYF_4$ seeds. For the Tm-doped UCNPs, more seeds lead to a smaller core-shell $NaYF_4@NaY_xYb_{0.96-x}F_4$:$Tm_{0.04}$ (x=0, 0.36, 0.66) nanoparticles (12 nm) if compared to the Er doped core-shell (22 nm) with less seeds.

The doping ratio variation of Yb (from 30% to 96%) didn't change the core-shell nanoparticles size distribution.

The details about the preparation of some exemplary Tm doped core-shell-shell UCNPs was as follows:

In a further embodiment, the synthesis of 6.0 nm $\beta$-$NaYF_4$ seed includes: 1.0 mmol $YCl_3.6H_2O$ aqueous solution was added into the mixture of 10 mL oleic acid and 10 mL octadecene, then the mixture was heated to 160° C. and kept for 30 min to remove water. The solution is cooled to <50° C., and 0.34 g $NH_4F$ and 2.03 g sodium oleate were quickly added into the reaction. The solution was heated to 120° C. and kept for 30 min, and then heated to 300° C. and maintained for 30 min at argon atmosphere. After the solution was cooled naturally, 25 mL ethanol was added, and the resulting mixture was centrifugally separated (12000 rpm for 10 min) to a compact pellet, and the supernatant was discarded. The products were collected and washed with cyclohexane and ethanol (40 mL, 1:1, v/v) three times. The product was stored in 20 mL cyclohexane. The final particle diameter was 6.0 nm±0.6 nm.

In another embodiment, the synthesis of $NaYF_4@NaY_xYb_{0.96-x}F_4$:$Tm_{0.04}$ includes: 0.40 mmol $RECl_3.6H_2O$ (96% $Yb^{3+}$, 4% $Tm^{3+}$; 36% $Y^{3+}$, 60% Yb, 4% $Tm^{3+}$; 66% $Y^{3+}$, 30% Yb, 4% $Tm^{3+}$) was added into 3 mL oleic acid and 8 mL octadecene in a 100 mL three-neck flask. The solution was heated to 160° C. to form a clear solution under argon atmosphere. After the mixture was cooled to room temperature, 10 mL of the prepared 6.0 nm $\beta$-$NaYF_4$ seed in cyclohexane and 5 mL methanol solution containing 1 mmol NaOH and 1.5 mmol $NH_4F$ were added into the reaction flask and stirred for 30 min. The solution was heated to 120° C. to remove low-boiling solvents for 30 min, and then heated to 300° C. and maintained for 1 h under argon atmosphere. The subsequent purification steps are the same as used for 6.0 nm $\beta$-$NaYF_4$ seed. The product was stored in 8 mL cyclohexane.

In a further embodiment, the synthesis of $NaYF_4@NaY_xYb_{0.96-x}F_4$:$Tm_{0.04}$@$NaYF_4$ (x=0, 0.36, 0.66) includes: 0.40 mmol $YCl_3.6H_2O$ was added into 3 mL oleic acid and 8 mL octadecene in a 100 mL three-neck flask. The solution was heated to 160° C. to form a clear solution under argon atmosphere. After the mixture was cooled to room temperature, the prepared $NaYF_4@NaY_xYb_{0.96-x}F_4$:$Tm_{0.04}$ in cyclohexane and 5 mL methanol solution containing 1 mmol NaOH and 1.5 mmol $NH_4F$ were added into the reaction flask and stirred for 30 min. The solution was heated to 120° C. to remove low-boiling solvents for 30 min, and then heated to 300° C. and maintained for 1 h under argon atmosphere. The subsequent purification steps are the same as used for 6.0 nm $\beta$-$NaYF_4$ seed. The product was stored in 8 mL cyclohexane.

FIGS. 19A-19E shows additional TEM images of $NaYF_4$ core (19A) and core-shell $NaYF_4@\ NaYb_{0.92}F_4$: $Er_{0.08}$ with different size (19B-19E), (19D) Final core-shell size as a function of the used core seeding volume and nonlinear fitting.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. An upconversion nanoparticle, comprising:
 a) an optically inert core comprising a hexagonal-phase nanoparticle seed crystal;

b) a hexagonal-phase first shell enveloping said core and including one or more rare earth ion doping species configured to provide upconversion; and c) an optically inert hexagonal-phase second shell enveloping said first shell.

2. The upconversion nanoparticle of claim 1, wherein said nanoparticle seed crystal comprises a $NaREF_4$ seed crystal, wherein said RE is selected from the group consisting of Y, Gd, Lu, Yb, Er, Tm, Ho, Pr, Nd, Eu, Tb, Dy, Ce, Sm, and La.

3. The upconversion nanoparticle of claim 1, wherein said nanoparticle seed crystal has a size in a range of 2-8 nm.

4. The upconversion nanoparticle of claim 1, wherein said first shell comprises a size-tunable and optically active $NaRE1F_4$: x % RE2 material, wherein said RE1 is selected from the group consisting of Y, Gd, Lu, Yb, Er, Tm, Ho, Pr, Nd, Eu, Tb, Dy, Ce, Sm, and La, wherein said RE2 is selected from the group consisting of Y, Gd, Lu, Yb, Er, Tm, Ho, Pr, Nd, Eu, Tb, Dy, Ce, Sm, and La, and wherein said x=0-100.

5. The upconversion nanoparticle of claim 1, wherein said first shell has a thickness in a range of 1-50 nm.

6. The upconversion nanoparticle of claim 1, wherein said second shell comprises an inert NaREF4 second shell, wherein said RE is selected from the group consisting of Y, Gd, Lu, and La.

7. The upconversion nanoparticle of claim 1, wherein said second shell has a thickness in a range of 1-25 nm.

8. A method of fabricating an upconversion nanoparticle, comprising:

a) synthesizing an optically inert hexagonal-phase core comprising a nanoparticle seed crystal;

b) synthesizing a hexagonal-phase first shell on said core including one or more rare earth ion doping species configured to provide upconversion; and c) synthesizing an optically inert hexagonal-phase second shell on said first shell;

wherein said nanoparticle seed crystal comprises NaREF4, wherein said RE is selected from the group consisting of Y, Gd, Lu, Yb, Er, Tm, Ho, Pr, Nd, Eu, Tb, Dy, Ce, Sm, and La.

9. The upconversion nanoparticle of claim 1, wherein the first shell includes a rare-earth doped $NaY_{1-x}Yb_xF_4$ composition, wherein x is in a range from 0.3 to 0.96.

10. The method of claim 8, wherein the first shell includes a rare-earth doped $NaY_{1-x}Yb_xF_4$ composition, wherein x is in a range from 0.3 to 0.96.

* * * * *